(12) United States Patent
Park et al.

(10) Patent No.: US 9,614,161 B2
(45) Date of Patent: Apr. 4, 2017

(54) COMPOUND AND ORGANIC ELECTRONIC ELEMENT USING SAME

(71) Applicant: LG CHEM, LTD., Seoul (KR)

(72) Inventors: Tae Yoon Park, Daejeon (KR); Minseung Chun, Daejeon (KR); Dongheon Kim, Daejeon (KR); Jiyeon Ahn, Daejeon (KR); Hyoung Seok Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/380,893

(22) PCT Filed: Feb. 6, 2014

(86) PCT No.: PCT/KR2014/001020
§ 371 (c)(1),
(2) Date: Aug. 25, 2014

(87) PCT Pub. No.: WO2014/123369
PCT Pub. Date: Aug. 14, 2014

(65) Prior Publication Data
US 2015/0340620 A1    Nov. 26, 2015

(30) Foreign Application Priority Data

Feb. 6, 2013 (KR) .................. 10-2013-0013211

(51) Int. Cl.
*H01L 51/50* (2006.01)
*H01L 51/00* (2006.01)
(Continued)

(52) U.S. Cl.
CPC ........ *H01L 51/0067* (2013.01); *C07D 405/14* (2013.01); *C07D 409/14* (2013.01);
(Continued)

(58) Field of Classification Search
None
See application file for complete search history.

(56) References Cited

U.S. PATENT DOCUMENTS 8,952,364 B2   2/2015   Lai et al.
8,975,314 B2   3/2015   Amasaki et al.
(Continued)

FOREIGN PATENT DOCUMENTS

JP   2013-075841 A   4/2013
JP   2014-103104 A   6/2014
(Continued)

OTHER PUBLICATIONS

Oyston et al., Enhanced electron injection and efficiency in blended-layer organic light diodes with aluminum cathodes: new 2,5-diaryl-1,3,4-oxadiazole-fluorene hybrids incorporating pyridine units, 2005, Journal of Materials Chemistry, vol. 15, pp. 5164-5173.*

(Continued)

*Primary Examiner* — Gregory Clark
(74) *Attorney, Agent, or Firm* — Dentons US LLP

(57) ABSTRACT

The present specification relates to an organic electronic device in which a new compound, which can improve the life span, the efficiency, the electrochemical stability and the thermal stability of the organic electronic device, is included in an organic material layer.

19 Claims, 3 Drawing Sheets

(51) Int. Cl.
*C07D 405/14* (2006.01)
*C09K 11/06* (2006.01)
*C07D 409/14* (2006.01)

(52) U.S. Cl.
CPC .......... *C09K 11/06* (2013.01); *H01L 51/0073* (2013.01); *H01L 51/0074* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *H01L 51/5012* (2013.01); *H01L 51/5048* (2013.01); *H01L 51/5072* (2013.01); *H01L 51/5092* (2013.01); *H01L 51/5096* (2013.01)

(56) References Cited

U.S. PATENT DOCUMENTS

| | | |
|---|---|---|
| 2006/0216411 A1 | 9/2006 | Steudel et al. |
| 2008/0111473 A1 | 5/2008 | Kawamura et al. |
| 2009/0058276 A1* | 3/2009 | Holliday ............ H01L 51/0036 313/504 |
| 2011/0196158 A1 | 8/2011 | Zheng |
| 2012/0226046 A1 | 9/2012 | Zheng et al. |
| 2012/0286249 A1 | 11/2012 | Lee et al. |
| 2014/0183422 A1 | 7/2014 | Stoessel et al. |

FOREIGN PATENT DOCUMENTS

| | | |
|---|---|---|
| JP | 2014-529586 A | 11/2014 |
| JP | 2014-535173 A | 12/2014 |
| KR | 10-2000-0051826 A | 8/2000 |
| KR | 10-2006-0085243 A | 7/2006 |
| KR | 10-2007-0088728 A | 8/2007 |
| KR | 2009-0008737 A | 1/2009 |
| KR | 10-2010-0077675 A | 7/2010 |
| KR | 10-2010-0094415 A | 8/2010 |
| KR | 10-2012-0127683 A | 11/2012 |
| WO | 2009-026377 A1 | 2/2009 |
| WO | 2012/119111 A1 | 9/2012 |

OTHER PUBLICATIONS

Lutz (Archic der Pharmazi, 1991) [SYN abstract only].*

* cited by examiner

COMPOUND AND ORGANIC ELECTRONIC ELEMENT USING SAME

This application is a National Stage Application of International Patent Application No. PCT/KR2014/001020, filed on Feb. 6, 2014, which claims the benefit of Korean Patent Application No. 10-2013-0013211, filed on Feb. 6, 2013 in the Korean Intellectual Property Office, all of which are incorporated herein by reference in their entirety.

TECHNICAL FIELD

The present specification relates to an organic electronic device in which a new compound, which can improve a life span, an efficiency, an electrochemical stability and a thermal stability of the organic electronic device, is included in an organic material layer.

BACKGROUND ART

An organic electronic device means a device that needs charge exchanges between an electrode and an organic material using holes and/or electrons. An organic electronic device can be categorized into two main groups depending on a operation principle. First is an electric device in which excitons form in an organic material layer by the photons brought into the device from an external light source, these excitons are separated into electrons and holes, and these electrons and holes are used as a current source (voltage source) by being transferred to different electrodes. Second is an electronic device in which holes and/or electrons are injected to an organic material semiconductor that forms an interface with an electrode by applying voltage or current to two or more electrodes, and the device is operated by the injected electrons and holes.

Examples of an organic electronic device include an organic light emitting device, an organic solar cell, an organic photo conductor (OPC), an organic transistor, and the like, and these all need a hole injection or transfer material, an electron injection or transfer material, or a light emitting material for the driving of the device. Hereinafter, an organic light emitting device will be described in detail, however, in the organic electronic devices, the hole injection or transfer material, the electron injection or transfer material, or the light emitting material is used under similar principles.

An organic light emission phenomenon generally refers to a phenomenon that converts electric energy to light energy using an organic material. An organic electronic device using an organic light emission phenomenon typically has a structure that includes an anode, a cathode, and an organic material layer therebetween. Herein, the organic material layer is usually formed as a multilayer structure formed with different materials in order to improve an efficiency and a stability of an organic electronic device, and for example, may be formed with a hole injection layer, a hole transfer layer, a light emitting layer, an electron transfer layer, an electron injection layer, and the like. In the structure of such an organic electronic device, holes from an anode and electrons from a cathode flow into the organic material layer when voltage is applied between the two electrodes, excitons form when the injected electrons and holes are combined, and light emits when these excitons fall back to a ground state. Such an organic electronic device has been known to have characteristics such as spontaneous light emission, high brightness, high efficiency, low driving voltage, wide viewing angle, high contrast and quick response.

In an organic electronic device, a material used as an organic material layer can be categorized into a light emitting material and a charge transfer material, for example, a hole injection material, a hole transfer material, an electron transfer material, an electron injection material and the like, depending on the function. In addition, a light emitting material can be categorized into, depending on a light emitting color, a blue, a green and a red light emitting material, and a yellow and an orange light emitting material to obtain better natural color. Meanwhile, when only one material is used as a light emitting material, problems occur such that a maximum light emitting wavelength moves to a long wavelength due to the interaction between molecules, color purity is reduced, or an efficiency of the device is reduced due to a light emission reduction effect. Therefore, a host/dopant-based material may be used as a light emitting material in order to increase color purity and increase light emission efficiency through the energy transfer.

In order for an organic electronic device to fully exhibit excellent characteristics described above, materials that form an organic material layer in the device, for example, a hole injection material, a hole transfer material, a light emitting material, an electron transfer material, an electron injection material, and the like, need to be supported by stable and efficient materials first, however, the development of stable and efficient materials of an organic material layer for an organic electronic device has not been sufficient so far. Therefore, there have been continuous demands for the development of new materials, and the needs for the development of such materials also apply to other organic electronic devices described above.

DISCLOSURE

Technical Problem

In view of the above, an objective of the present application is to provide an organic electronic device that includes a compound satisfying conditions required for the materials usable in an organic electronic device, such as life span, efficiency, electrochemical stability and thermal stability, and having a chemical structure that can perform various roles required in an organic electronic device depending on substituents.

Technical Solution

The present specification provides a compound represented by the following Chemical Formula 1.

[Chemical Formula 1]

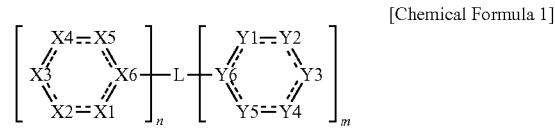

In Chemical Formula 1,
X1 to X5 and Y1 to Y5 are each independently C-Cy, N-Cy, CR or N,
X6 and Y6 are each independently C or N,
at least one of X1 to X6 is N, at least one of X1 to X5 is C-Cy or N-Cy,
at least one of Y1 to Y6 is N, at least one of Y1 to Y5 is C-Cy or N-Cy,
when X6 is N, at least one of X1 to X5 is C-Cy or CR,
when Y6 is N, at least one of Y1 to Y5 is C-Cy or CR, Cy is a substituted or unsubstituted heteroring group including one or more of O and S atoms, R is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted fluorenyl group, n and m are each independently an integer of 1 to 5, n+m is 2 to 6, and L is a substituted or unsubstituted aryl group having the valency of n+m.

In addition, the present specification provides an organic electronic device that includes a first electrode, a second electrode, and one or more organic material layers disposed between the first electrode and the second electrode, wherein the one or more organic material layers include the compound described above.

Advantageous Effects

An organic electronic device according to one embodiment of the present specification has advantages in that a life span characteristics are improved.

An organic electronic device according to one embodiment of the present specification has advantages in that a luminance efficiency is improved.

An organic electronic device according to one embodiment of the present specification has advantages in that a driving voltage is low.

An organic electronic device according to one embodiment of the present specification has advantages in that an electrochemical stability and a thermal stability are improved.

MODE FOR DISCLOSURE

Figure 1:
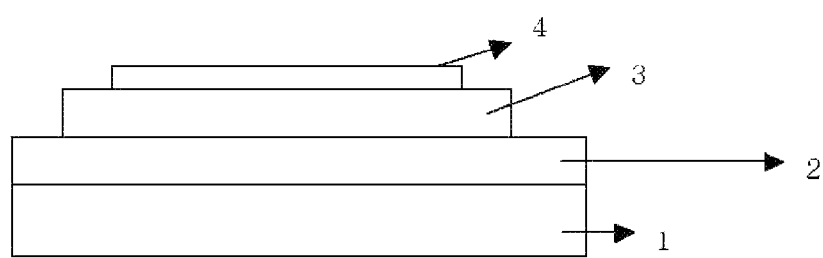
FIG. 1 shows an example of an organic electronic device formed with a substrate (1), an anode (2), a light emitting layer (3) and a cathode (4) by a diagram.

Hereinafter, the present specification will be described in more detail.

The present specification provides a heterocyclic compound.

The heterocyclic compound may be represented by the following Chemical Formula 1.

[Chemical Formula 1]

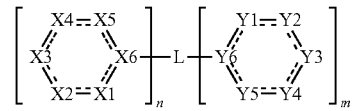

In Chemical Formula 1,

X1 to X5 and Y1 to Y5 are each independently C-Cy, N-Cy, CR or N,

X6 and Y6 are each independently C or N, at least one of X1 to X6 is N, at least one of X1 to X5 is C-Cy or N-Cy, at least one of Y1 to Y6 is N, at least one of Y1 to Y5 is C-Cy or N-Cy, When X6 is N, at least one of X1 to X5 is C-Cy or CR, When Y6 is N, at least one of Y1 to Y5 is C-Cy or CR, Cy is a substituted or unsubstituted heteroring group including one or more of O and S atoms, R is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted fluorenyl group, n and m are each independently an integer of 1 to 5, n+m is 2 to 6, and L is a substituted or unsubstituted aryl group having the valency of n+m.

In Chemical Formula 1, Cy may be a substituted or unsubstituted thiophene group; a substituted or unsubstituted furan group; a substituted or unsubstituted benzothiophene group; a substituted or unsubstituted benzofuran group; a substituted or unsubstituted dibenzothiophene group; or a substituted or unsubstituted dibenzofuran group.

In Chemical Formula 1, Cy may be a substituted or unsubstituted dibenzothiophene group; or a substituted or unsubstituted dibenzofuran group.

Specifically, Cy may be represented by the following chemical formula.

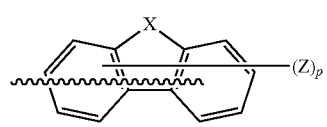

Herein, X is O or S, p is an integer of 0 to 7, and

Zs are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted fluorenyl group.

In Chemical Formula 1, Cy may be represented by any one of the following chemical formulae.

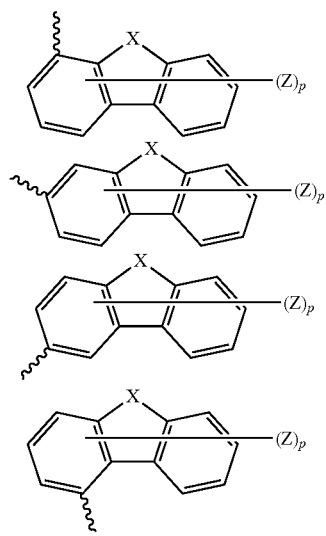

Herein, X is O or S, p is an integer of 0 to 7, and

Zs are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted fluorenyl group.

In Chemical Formula 1,

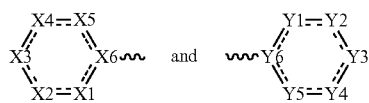

may be each independently represented by any one of the following chemical Formulae.

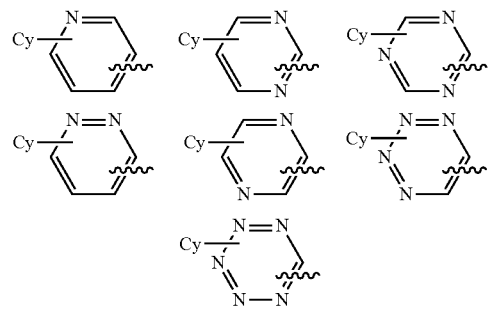

Herein, Cy is the same as that defined in Chemical Formula 1.

In Chemical Formula 1, any one or two of X1 to X6 may be N or N-Cy. In this case,

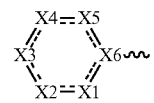

may be represented by any one of the following chemical formulae.

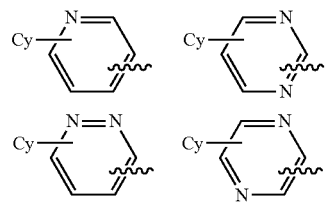

Herein, Cy is the same as that defined in Chemical Formula 1.

In Chemical Formula 1, any one or two of Y1 to Y6 may be N or N-Cy. In this case,

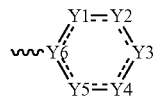

may be represented by any one of the following chemical formulae.

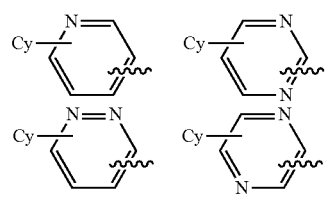

In Chemical Formula 1,

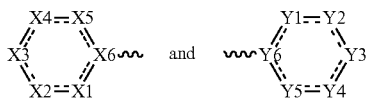

may be the same as each other.

In Chemical Formula 1,

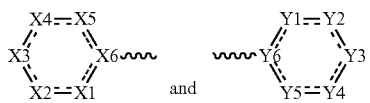

may be symmetrical to each other. Specifically, the compounds may be point symmetrical or line symmetrical with L as the center.

In Chemical Formula 1, L may be a substituted or unsubstituted phenyl group having the valency of n+m; a substituted or unsubstituted biphenyl group having the valency of n+m; a substituted or unsubstituted terphenyl group having the valency of n+m; a substituted or unsubstituted stilbene group having the valency of n+m; a substituted or unsubstituted naphthyl group having the valency of n+m; a substituted or unsubstituted anthracenyl group having the valency of n+m; a substituted or unsubstituted phenanthrene group having the valency of n+m; a substituted or unsubstituted pyrenyl group having the valency of n+m; a substituted or unsubstituted perylenyl group having the valency of n+m; a substituted or unsubstituted crycenyl group having the valency of n+m; or a substituted or unsubstituted fluorene group having the valency of n+m.

In Chemical Formula 1, L may be a substituted or unsubstituted phenyl group having the valency of n+m; a substituted or unsubstituted naphthyl group having the valency of n+m; or a substituted or unsubstituted fluorene group having the valency of n+m.

In the present specification, since n+m is 2 to 6, a substituent having the valency of n+m means a divalent substituent, a trivalent substituent, a tetravalent substituent, a pentavalent substituent or a hexavalent substituent.

In Chemical Formula 1, L may be represented by any one of the following chemical formulae.

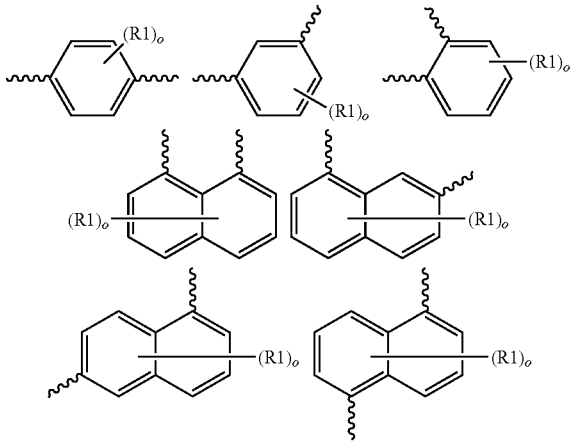

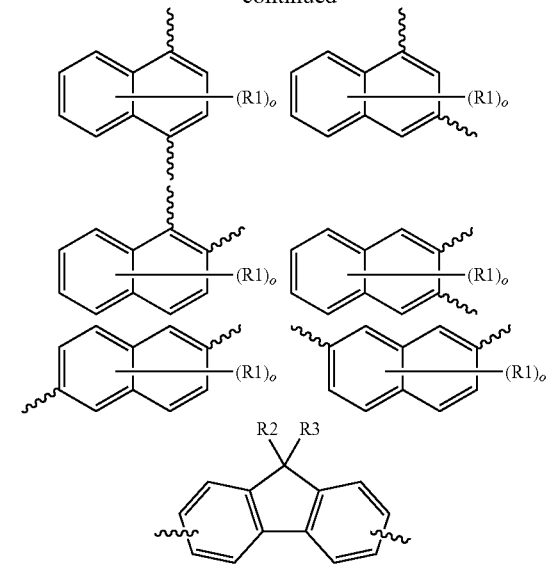

Herein, o is an integer of 0 to 4,

R1s may be the same as or different from each other, and are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted heteroring group; or a substituted or unsubstituted fluorenyl group, R2 and R3 are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted heteroring group; or a substituted or unsubstituted fluorenyl group, and R1 to R3 may form an aliphatic or a hetero fused ring with groups adjacent to each other.

In Chemical Formula 1, n and m may be 1.

In Chemical Formula 1, Cy is a substituted or unsubstituted dibenzothiophene group; or a substituted or unsubstituted dibenzofuran group, and one or two of X1 to X6 is N or N-Cy, and one or two of Y1 to Y6 is N or N-Cy.

In Chemical Formula 1, Cy is a substituted or unsubstituted dibenzothiophene group; or a substituted or unsubstituted dibenzofuran group, one or two of X1 to X6 is N or N-Cy, and one or two of Y1 to Y6 is N or N-Cy, and L is a substituted or unsubstituted phenyl group having the valency of n+m; a substituted or unsubstituted naphthyl group having the valency of n+m; or a substituted or unsubstituted fluorene group having the valency of n+m.

In Chemical Formula 1, Cy is a substituted or unsubstituted dibenzothiophene group; or a substituted or unsubstituted dibenzofuran group, one or two of X1 to X6 is N or N-Cy, one or two of Y1 to Y6 is N or N-Cy, L is a substituted or unsubstituted phenylene group; a substituted or unsubstituted divalent naphthyl group; or a substituted or unsubstituted divalent fluorene group, and n and m are 1.

In the compound according to the present specification, substituents of Chemical Formula 1 are more specifically described as follows.

In the present specification, the term "substituted or unsubstituted" means being substituted with one or more substituents selected from the group consisting of deuterium, a halogen group, an alkyl group, an alkenyl group, an amine group, an alkoxy group, a silyl group, an arylalkenyl group, an aryl group, a heteroring group, a carbazole group, an arylamine group, a heteroarylamine group, a fluorenyl group unsubstituted or substituted with an aryl group, and a nitrile group, or means "H" having no substituents.

In the present specification, the halogen group includes fluorine, chlorine, bromine, iodine and the like, but is not limited thereto.

In the present specification, the alkyl group may be linear or branched, and although not particularly limited, the number of carbon atoms is preferably 1 to 12. Specific examples thereof include a methyl group, an ethyl group, a propyl group, an isopropyl group, a butyl group, a t-butyl group, a pentyl group, a hexyl group, a heptyl group and the like, but are not limited thereto.

In the present specification, the alkenyl group may be linear or branched, and although not particularly limited, the number of carbon atoms is preferably 2 to 12. Specific examples thereof preferably include a butenyl group; a pentenyl group; or an alkenyl group in which an aryl group is linked such as a stylbenyl group or a styrenyl group, but are not limited thereto.

In the present specification, the alkoxy group preferably has 1 to 12 carbon atoms, and more specifically, includes a methoxy group, an ethoxy group, an isopropyloxy group and the like, but is not limited thereto.

In the present specification, the aryl group or the arylene group may be monocyclic or multicyclic, and although not particularly limited, the number of carbon atoms is preferably 6 to 40. Examples of the monocyclic aryl group include a phenyl group, a biphenyl group, a terphenyl group, stilbene and the like, and examples of the multicyclic aryl group include a naphthyl group, an anthracenyl group, a phenanthrene group, a pyrenyl group, a perylenyl group, a crycenyl group, a fluorene group and the like, but the examples are not limited thereto.

In addition, examples of the monocyclic arylene group include a phenylene group, a biphenylene group, a terphenylene group, divalent stilbene and the like, and examples of the multicyclic arylene group include a divalent naphthyl group, a divalent anthracenyl group, a divalent phenanthrene group, a divalent pyrenyl group, a divalent perylenyl group, a divalent crycenyl group, a divalent fluorene group and the like, but the examples are not limited thereto.

In the present specification, the fluorenyl group has a structure in which two cyclic organic compounds are linked through one atom, and examples thereof include

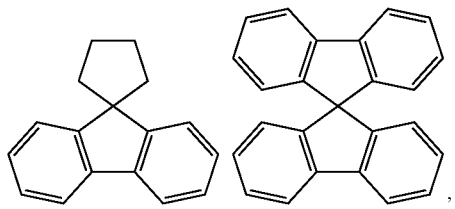

and the like.

In the present specification, the fluorenyl group includes the structure of an open fluorenyl group, and herein, the open fluorenyl group has a structure in which the linkage of one ring compound is broken in the structure of two ring compounds linked through one atom, and examples thereof include

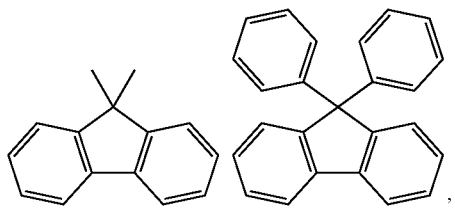

and the like.

In the present specification, the number of carbon atoms of the amine group is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a phenylnaphthylamine group, a ditolylamine group, a phenyltolylamine group, a triphenylamine group and the like, but are not limited thereto.

In the present specification, examples of the arylamine group mean a substituted or unsubstituted monocyclic diarylamine group, a substituted or unsubstituted multicyclic diarylamine group or a substituted or unsubstituted monocyclic and multicyclic diarylamine group.

In the present specification, the heteroring group is a heteroring group that includes any one or more of O, N and S as a heteroatom, and although not particularly limited, the number of carbon atoms is preferably 2 to 60.

In the present specification, the heteroring group may be a heteroaryl group. Examples of the heteroaryl group include a thiophene group, a furan group, a pyrrole group, an imidazole group, a triazole group, an oxazole group, an oxadiazole group, a triazole group, a pyridyl group, a bipyridyl group, a triazine group, an acridyl group, a pyridazine group, a qinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a dibenzofuranyl group and the like, but are not limited thereto.

For example, the heteroaryl group is preferably a compound having the following structural formulae, however, the heteroaryl group is not limited thereto.

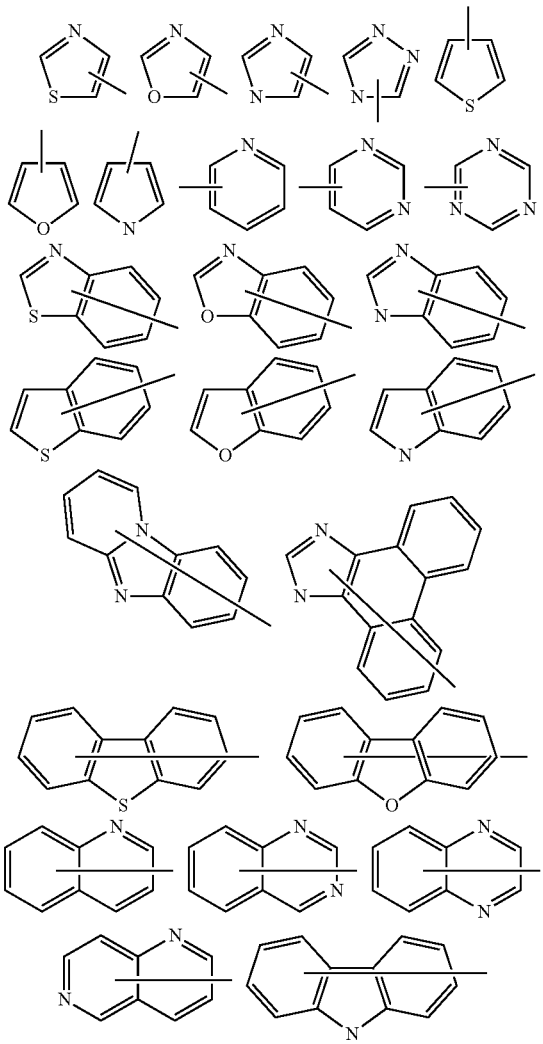

In one embodiment of the present specification, the compound represented by Chemical Formula 1 may be presented by any one of the following chemical formulae, however, the compound is not limited thereto.

Structural Formula 1

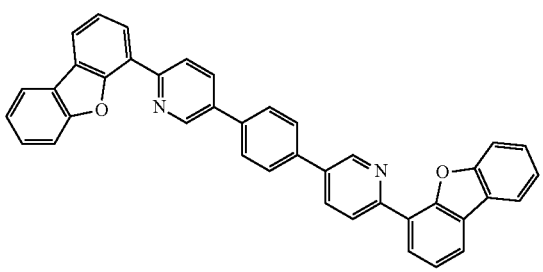

Structural Formula 2

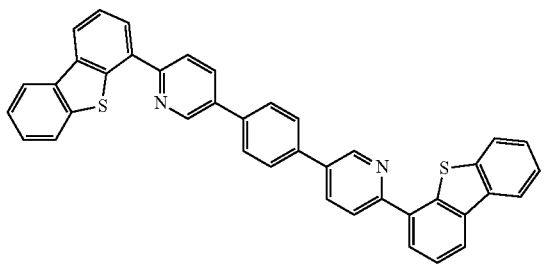

Structural Formula 3

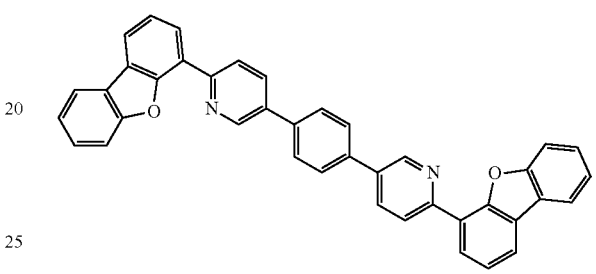

Structural Formula 4

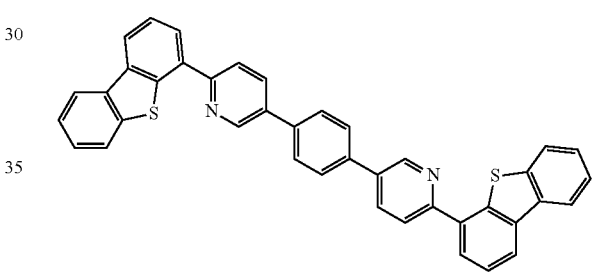

Structural Formula 5

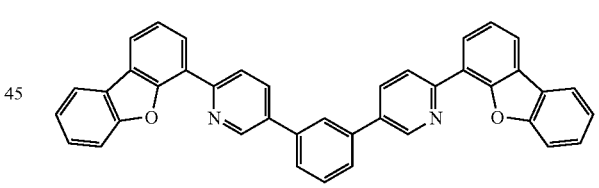

Structural Formula 6

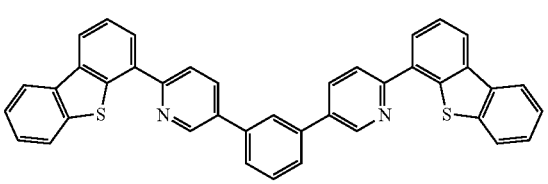

Structural Formula 7

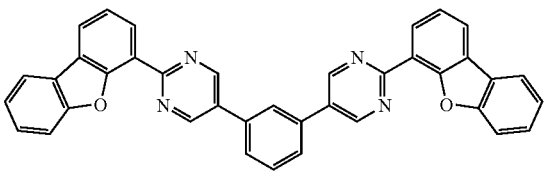

Structural Formula 8
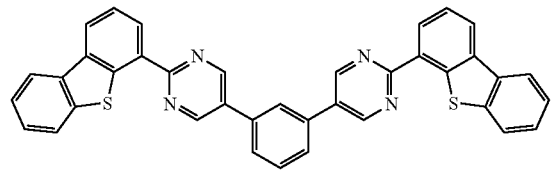
Structural Formula 9
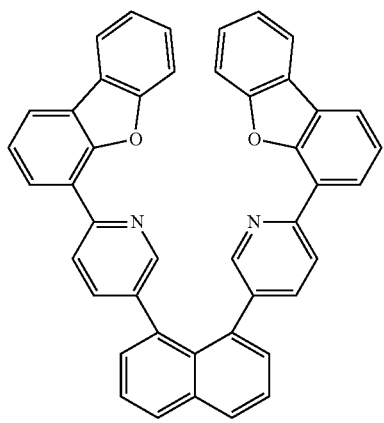
Structural Formula 10
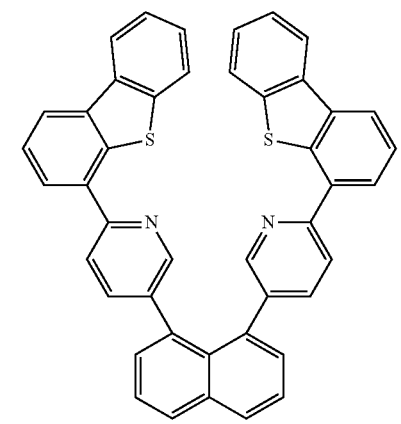
Structural Formula 11
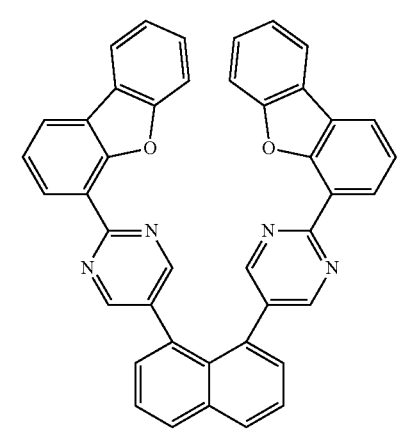
Structural Formula 12
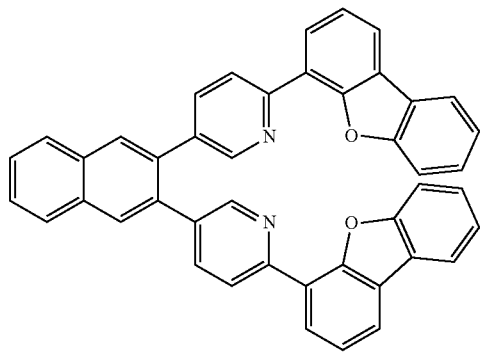
Structural Formula 13
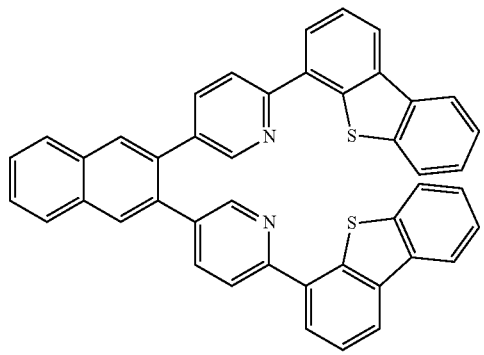
Structural Formula 14
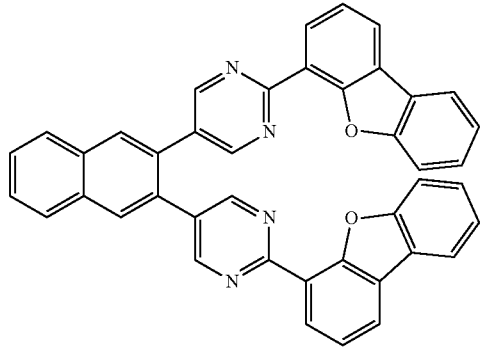
Structural Formula 15

Structural Formula 16
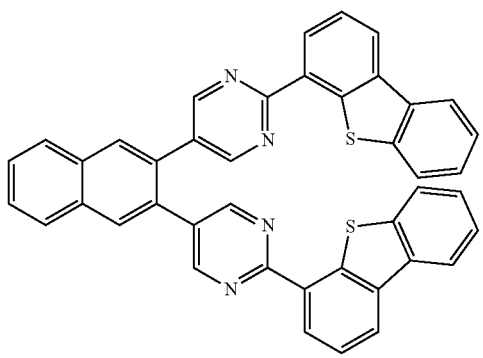
Structural Formula 17
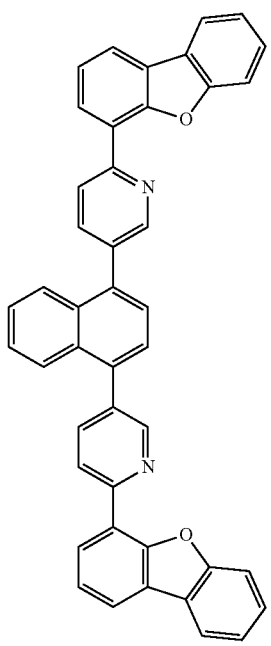
Structural Formula 18
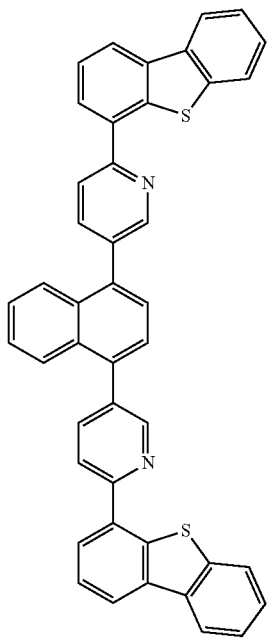
Structural Formula 19
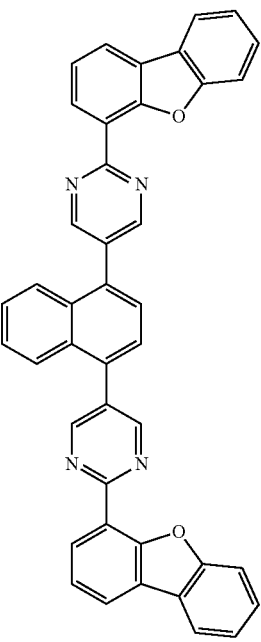
Structural Formula 20
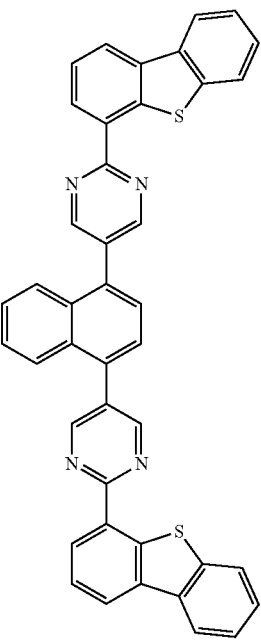

Structural Formula 21
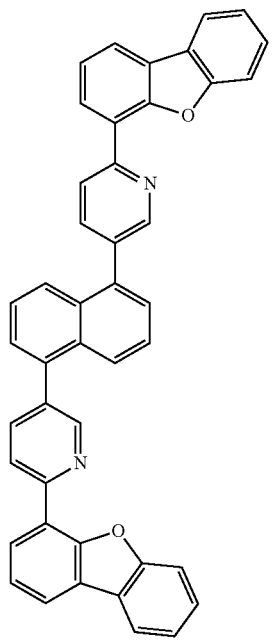
Structural Formula 23
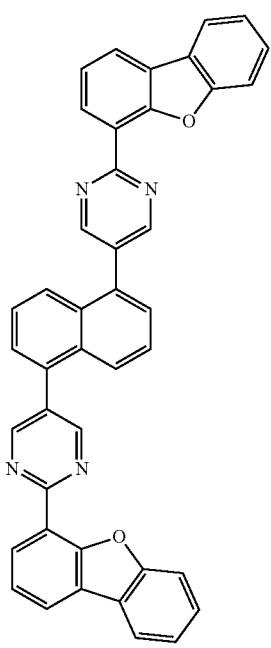
Structural Formula 22
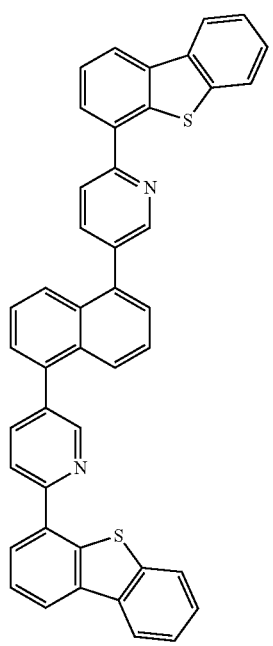
Structural Formula 24
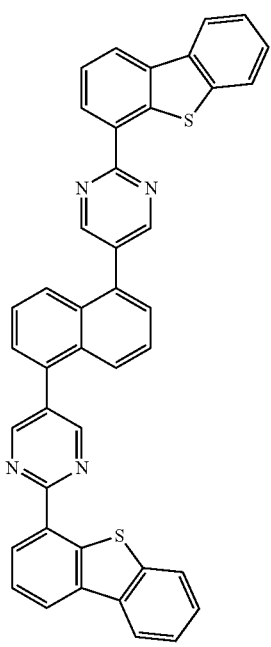

Structural Formula 25
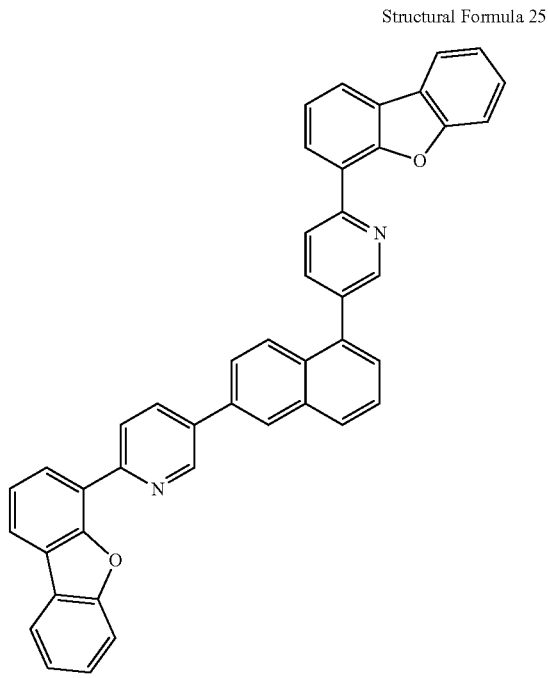
Structural Formula 26
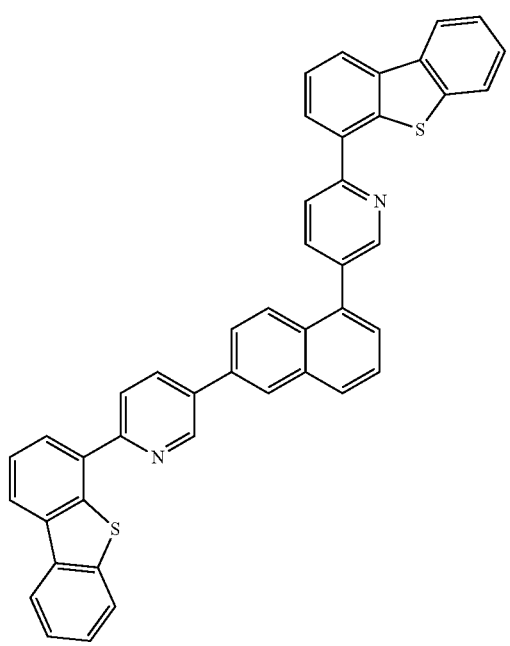
Structural Formula 27
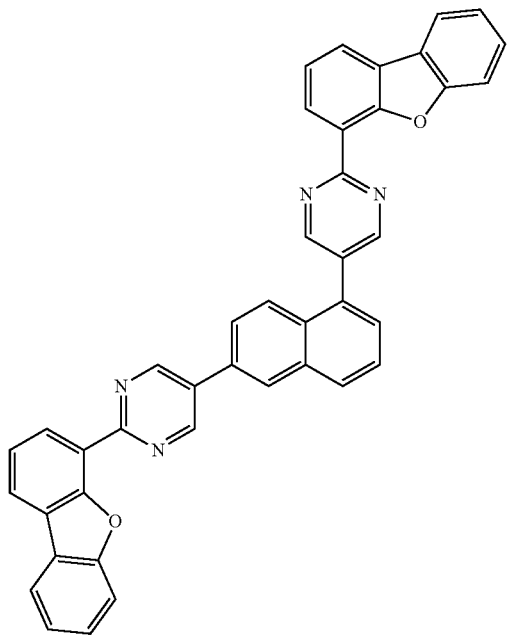
Structural Formula 28
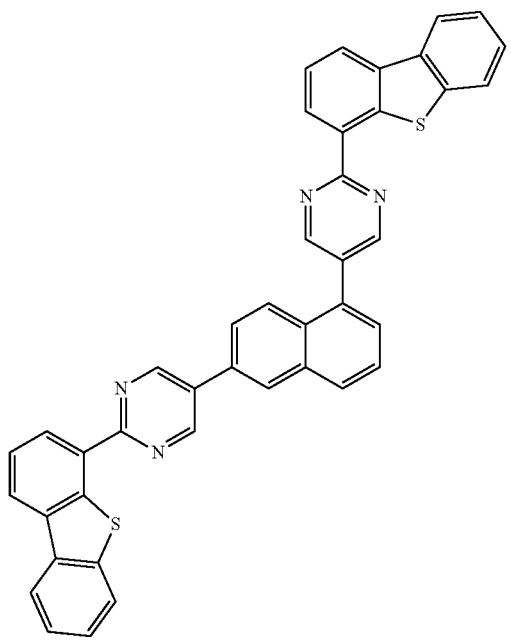
Structural Formula 29
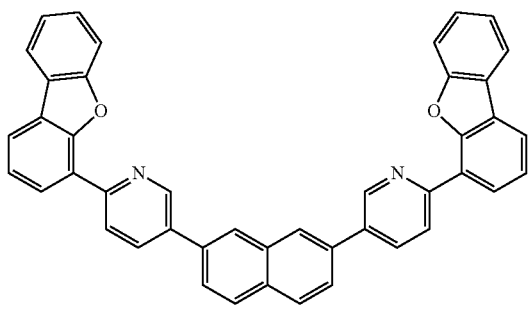

Structural Formula 30
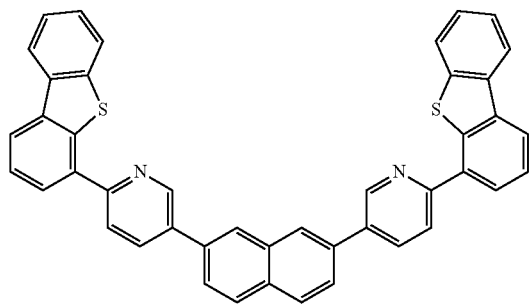
Structural Formula 31
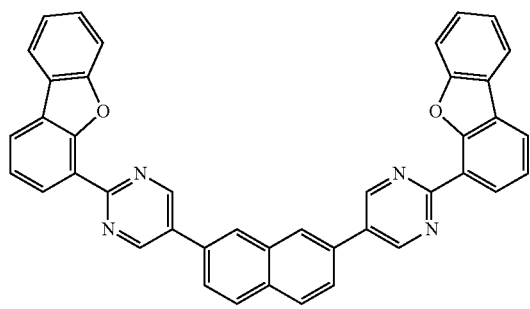
Structural Formula 32
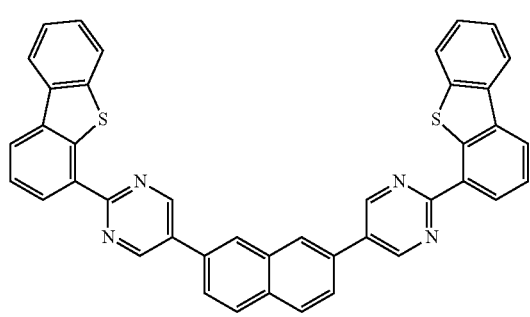
Structural Formula 33
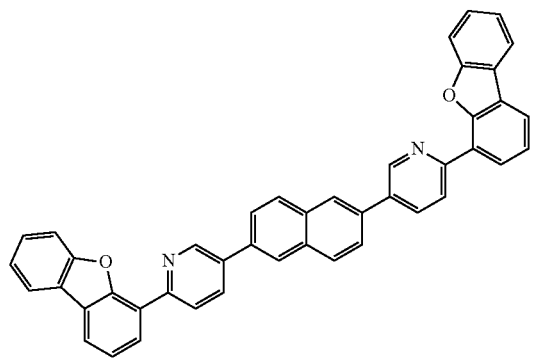
Structural 34
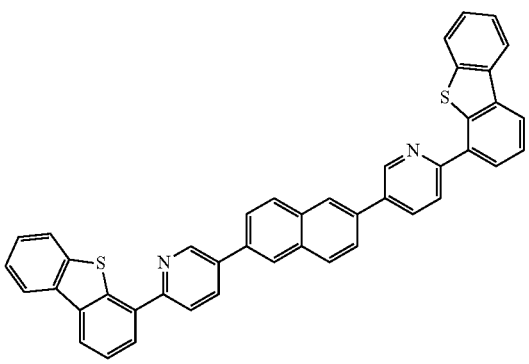
Structural 35
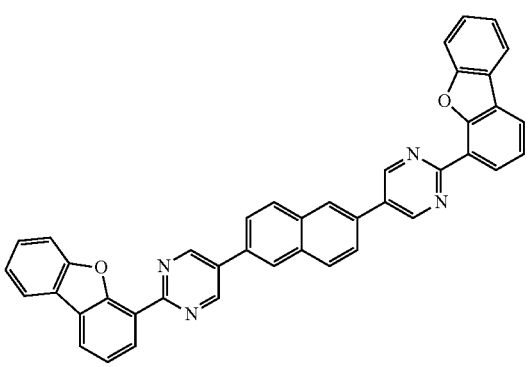
Structural Formula 36
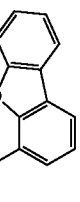
Structural Formula 37
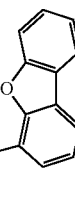
Structural Formula 38
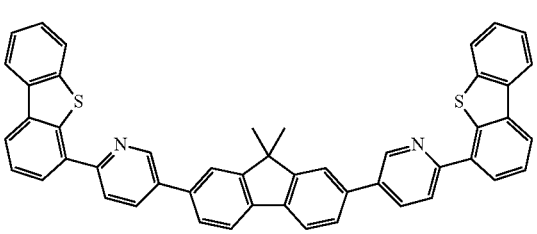

Structural Formula 39
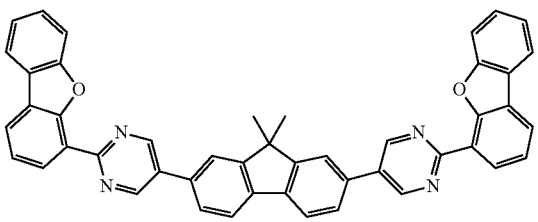
Structural Formula 40
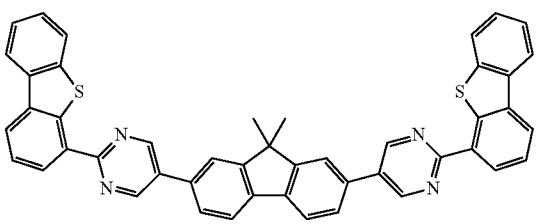
Structural Formula 41
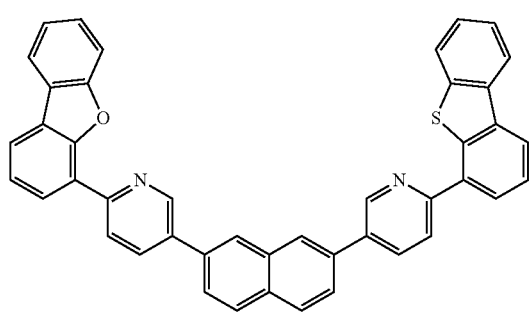
Structural Formula 42
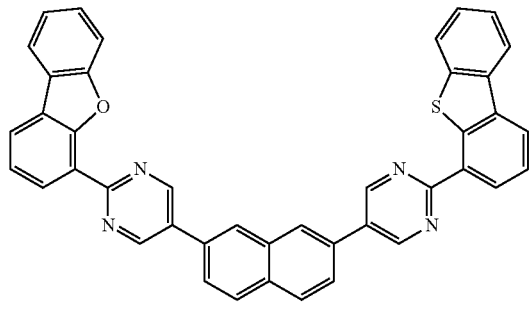
Structural Formula 43
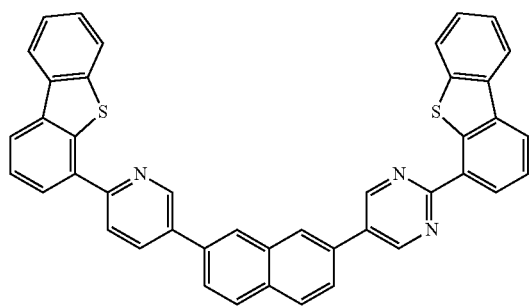
Structural Formula 44
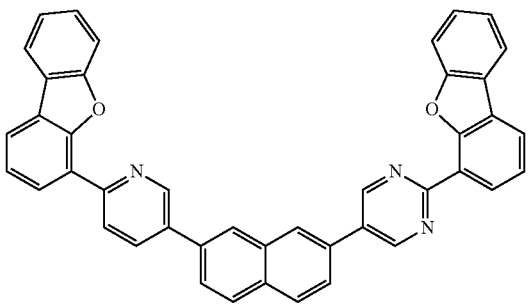
Structural Formula 45
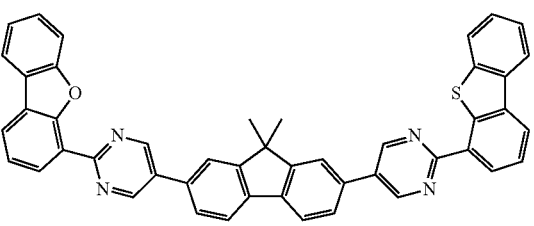
Structural Formula 46
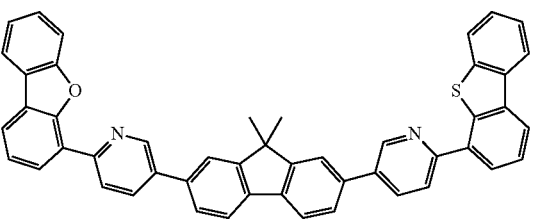
Structural Formula 47
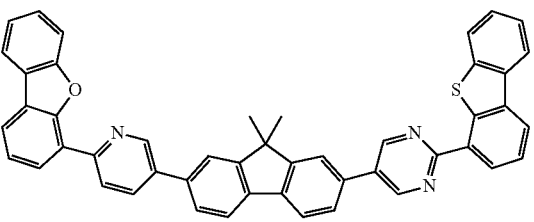
Structural Formula 48
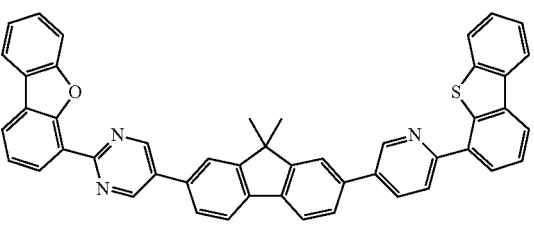

Structural Formula 49
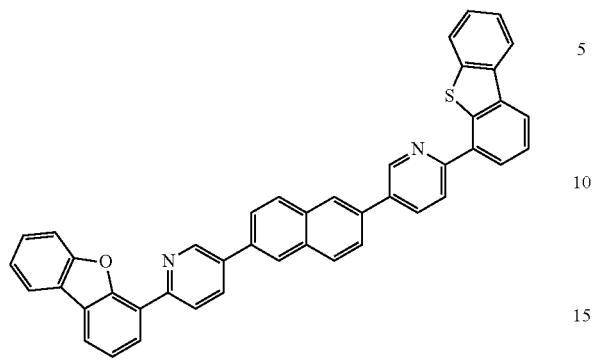
Structural Formula 50
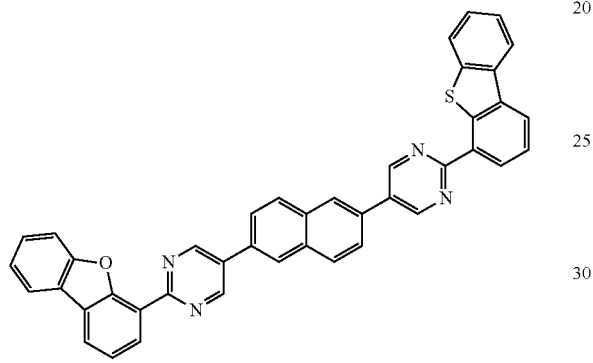
Structural Formula 51
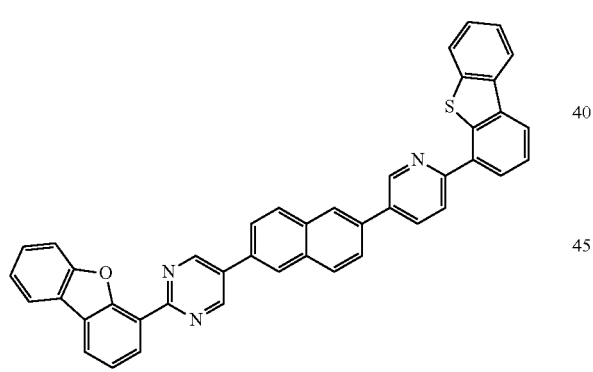
Structural Formula 52
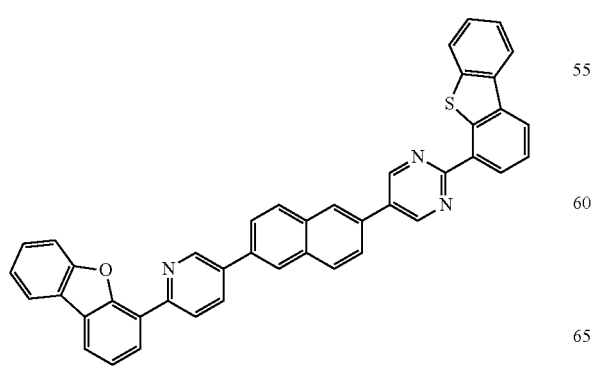
Structural Formula 53
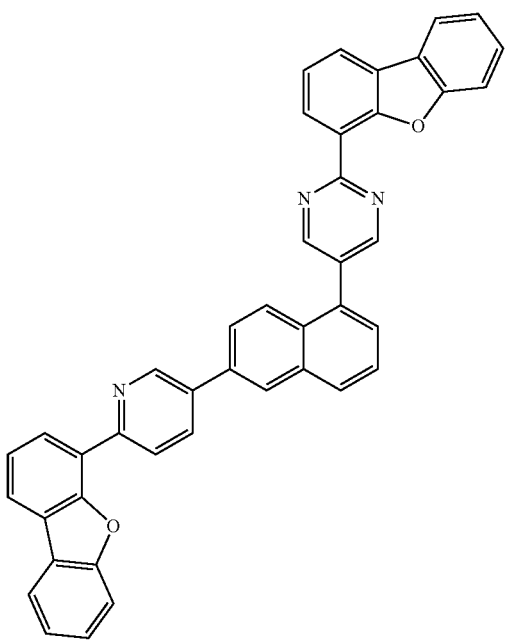
Structural Formula 54
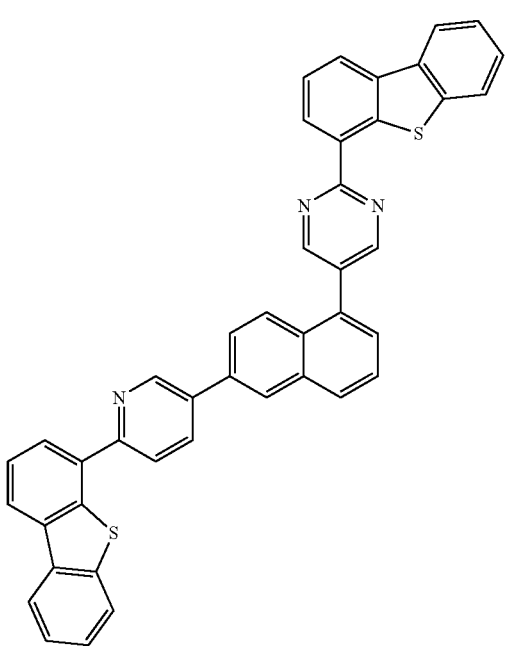

-continued
Structural Formula 55
Structural Formula 57
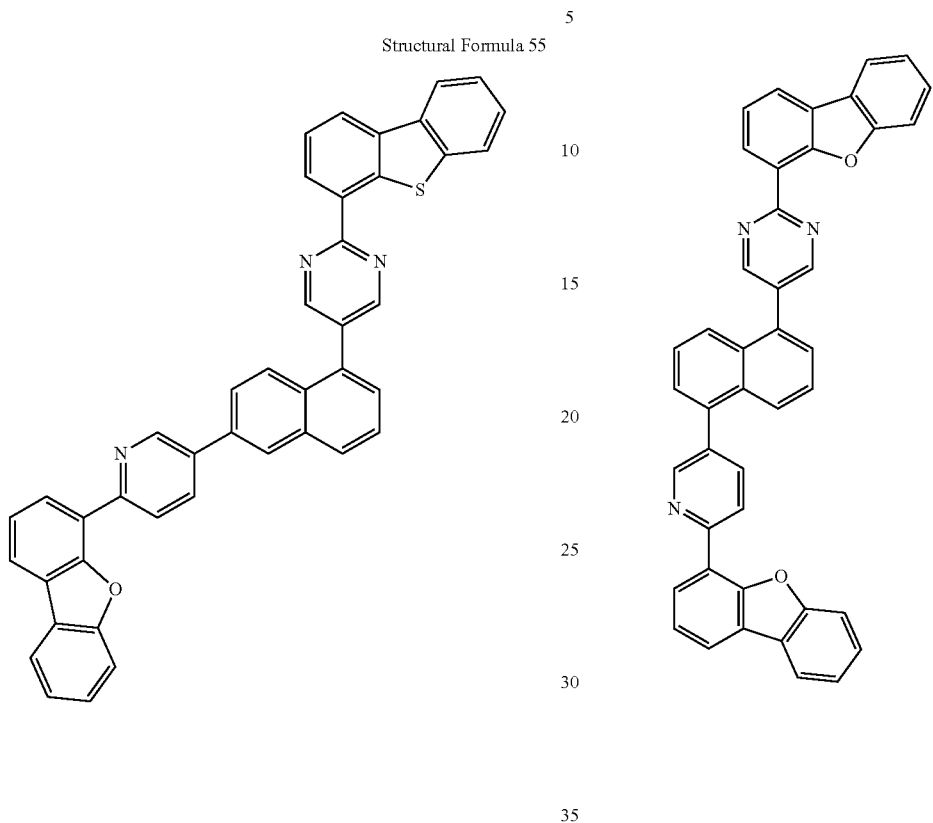
Structural Formula 56
Structural Formula 58
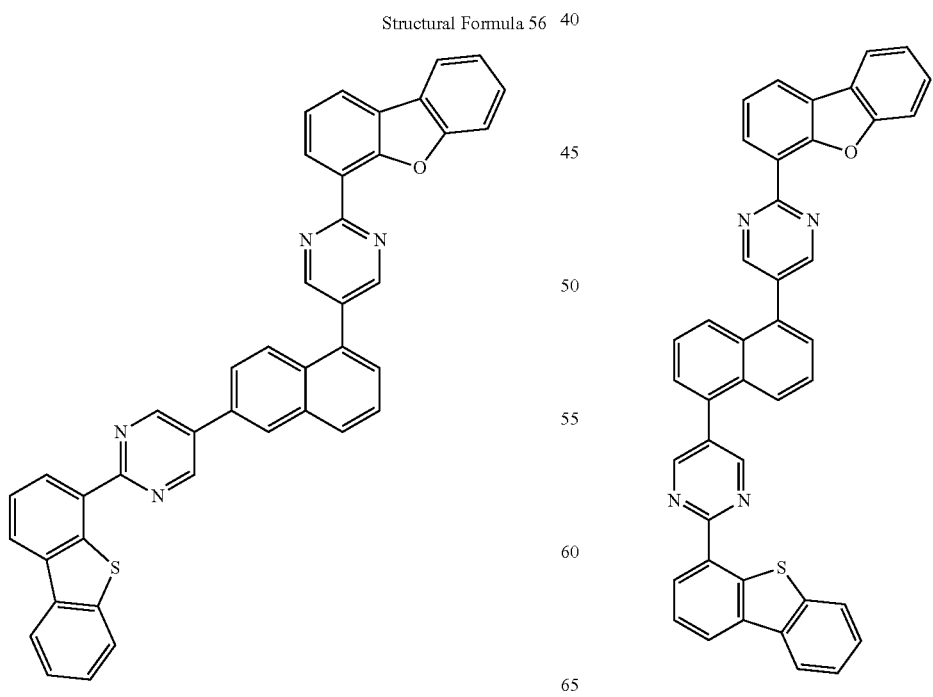

Structural Formula 59

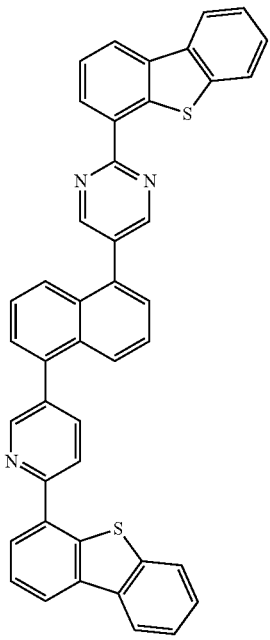

Structural Formula 60

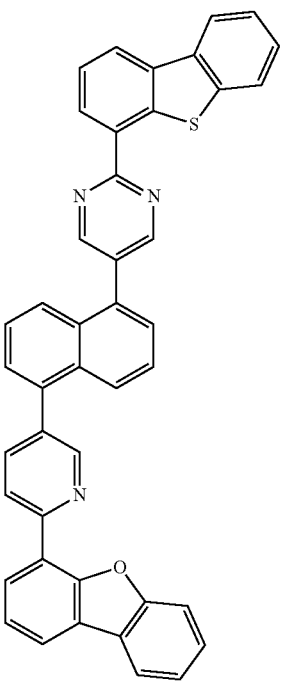

The new compounds according to the present specification have an advantage in that they have excellent thermal stability. As a result, the compounds have effects of being stable with respect to joule heating generated due to the movement of charges in an organic electronic device.

The new compounds according to the present specification have an advantage in that they have a deep HOMO level.

The new compounds according to the present specification have an advantage in that they have a high triplet state.

The new compounds according to the present specification have an advantage in that they have hole stability.

The new compounds according to the present specification can be used in an organic electronic device including a light emitting device either purely or by being mixed with impurities.

The new compounds according to the present specification may have an energy level suitable as a hole injection and/or a hole transfer material in an organic electronic device. In the present specification, a device having low driving voltage and high luminance efficiency can be obtained by selecting a compound having a suitable energy level depending on the substituents among the compounds described above, and using the compound in an organic electronic device.

In addition, by introducing various substituents to the core structure, the energy band gap can be finely adjusted, and meanwhile, characteristics at the interface between organic materials are improved, and therefore, the materials can have various applications.

Meanwhile, the compound represented by Chemical Formula 1 has excellent thermal stability due to its high glass transition temperature ($T_g$). This thermal stability enhancement becomes an important factor that provides a driving stability to a device.

The organic electronic device according to the present specification has advantages in that the luminance efficiency is improved, and a life span characteristics of a device are improved due to high thermal stability.

In addition, the organic electronic device according to the present specification includes a first electrode, a second electrode, and one or more organic material layers disposed between the first electrode and the second electrode, wherein the one or more organic material layers include the compound represented by Chemical Formula 1.

Examples of the organic electronic device include an organic light emitting device, an organic solar cell, an organic photo conductor (OPC), an organic transistor, and the like, but are not limited thereto.

The organic electronic device of the present specification may be prepared using common methods and materials of organic electronic devices except that the compound represented by Chemical Formula 1 described above is used to form one or more organic material layers.

For example, the organic electronic device according to the present specification may be manufactured by forming an anode through the deposition of a metal, a metal oxide having conductivity, or alloys thereof on a substrate using a physical vapor deposition (PVD) method such as sputtering or e-beam evaporation, forming an organic material layer that includes a hole injection layer, a hole transfer layer, a light emitting layer and an electron transfer layer thereon, and then depositing a material that can be used as a cathode thereon. In addition to this method, the organic electronic device may also be manufactured by consecutively depositing a cathode material, an organic material layer and an anode material on a substrate.

In addition, the organic material layer may be formed with less number of layers using a solvent process instead of a deposition method, for example, spin coating, dip coating, doctor blading, screen printing, ink jet printing or a thermal printing method, using various polymer materials.

The organic material layer of the organic electronic device of the present specification may be formed as a monolayer structure, but may be formed as a multilayer structure in which two or more organic material layers are laminated. For example, the organic electronic device of the present specification may have a structure including a hole injection layer, a hole transfer layer, a light emitting layer, an electron transfer layer, an electron injection layer, and the like as the organic material layer. However, the structure of the organic light emitting device is not limited thereto, and may include less number of organic material layers.

Therefore, in the organic electronic device of the present specification, the organic material layer may include one or more of a hole injection layer, a hole transfer layer, and a layer that injects and transfers holes at the same time, and one or more of the layers may include the compound represented by Chemical Formula 1.

In addition, the organic material layer may include a light emitting layer, and the light emitting layer may include the compound represented by Chemical Formula 1.

In addition, the organic material layer may include one or more of an electron blocking layer, an electron transfer layer, an electron injection layer, and a layer that injects and transfers electrons at the same time, and one or more of the layers may include the compound represented by Chemical Formula 1.

In addition, the compound of the present specification may be used as an organic material layer material, particularly, a hole injection layer material, a hole transfer layer material, a light emitting layer material, an electron transfer layer material, and the like, in an organic electronic device.

As the anode material, a material having large work function is normally preferable so that hole injection to the organic material layer can be smooth. Specific examples of the anode material that can be used in the present specification include metals such as vanadium, chromium, copper, zinc or gold, or alloys thereof; metal oxides such as zinc oxides, indium oxides, indium tin oxides (ITO) or indium zinc oxides (IZO); mixtures of metals and oxides such as ZnO:Al or $SnO_2$:Sb; conductive polymers such as poly[3,4-(ethylene-1,2-dioxy)thiophene] (PEDOT), polypyrrole and polyaniline, and the like, but are not limited thereto.

As the cathode material, a material having small work function is normally preferable so that electron injection to the organic material layer can be smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is a material that can favorably receive holes by injection from an anode, and the highest occupied molecular orbital (HOMO) of the hole injection material is preferably between the work function of an anode material and the HOMO of surrounding organic material layers. Specific examples of the hole injection material include a metal porphyrin, oligothiophene, an arylamine-based organic material, a hexanitrile hexaazatriphenylene-based organic material, a quinacridone-based organic material, a perylene-based organic material, anthraquinone, a polyaniline- and a polycompound-based conductive polymer, and the like, but are not limited thereto.

The hole transfer material is a material that can receive holes from an anode or a hole injection layer and move the holes to a light emitting layer, and a material having high mobility for holes is suitable. Specific examples thereof include an arylamine-based organic material, a conductive polymer, a block copolymer having conjugated parts and non-conjugated parts together, and the like, but are not limited thereto.

The light emitting material is a material that can emit light in a visible light region by receiving holes and electrons from a hole transfer layer and an electron transfer layer, respectively, and binding the holes and the electrons, and a material having favorable quantum efficiency for fluorescence or phosphorescence is preferable. Specific examples thereof include a 8-hydroxy-quinoline aluminum complex ($Alq_3$); a carbazole-based compound; a dimerized styryl compound; BAlq; a 10-hydroxybenzo quinoline-metal compound; a benzoxazole-, a benzthiazole- and a benzimidazole-based compound; a poly(p-phenylenevinylene) (PPV)-based polymer; a spiro compound; polyfluorene, rubrene, and the like, but are not limited thereto.

The electron transfer material is a material that can receive electrons from a cathode and move the electrons to a light emitting layer, and a material having high mobility for electrons is suitable. Specific examples thereof include an Al complex of 8-hydroxyquinoline; a complex including $Alq_3$; an organic radical compound; a hydroxyflavone-metal complex or the like, but are not limited thereto.

The organic electronic device according to the present specification may be a top-emission type, a bottom-emission type or a dual-emission type depending on the materials used.

The organic electronic device according to the present specification may be an organic light emitting device.

Figure 2:
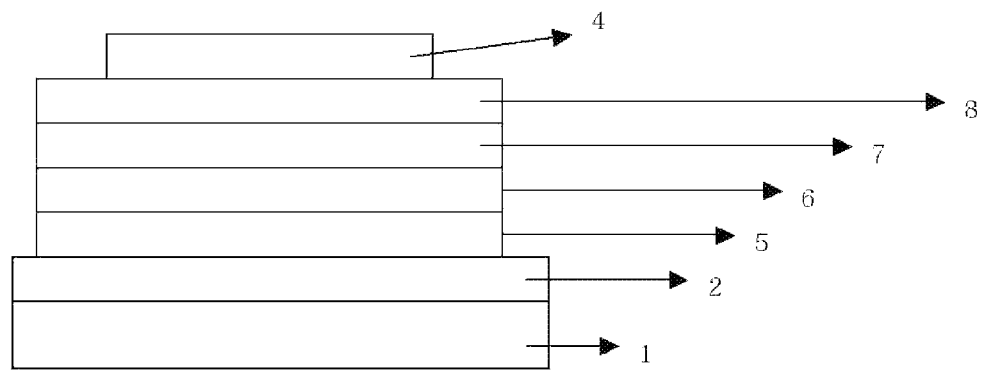
FIG. 2 shows an example of an organic electronic device formed with a substrate (1), an anode (2), a hole injection layer (5), a hole transfer layer (6), a light emitting layer (7), an electron transfer layer (8) and a cathode (4) by a diagram.
Figure 3:
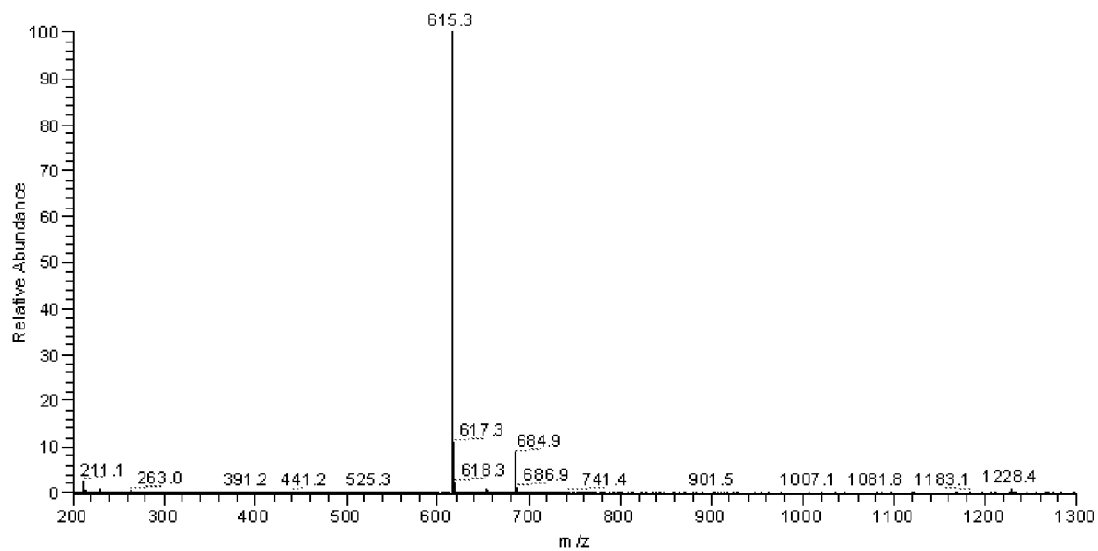
FIG. 3 is an NMR graph of the compound of Structural Formula 29 synthesized in Preparation Example 1.
Figure 4:
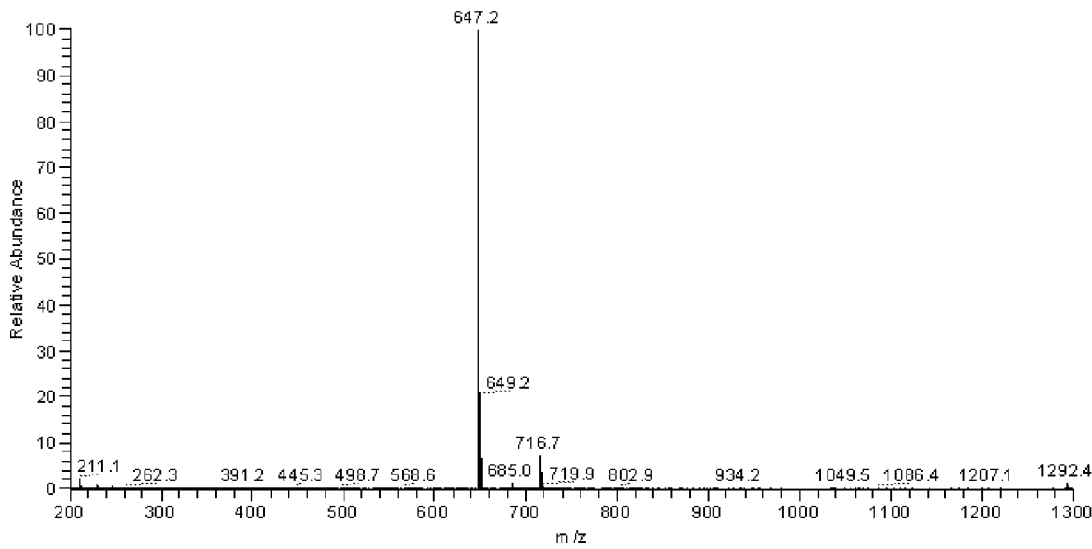
FIG. 4 is an NMR graph of the compound of Structural Formula 30 synthesized in Preparation Example 2.
Figure 5:
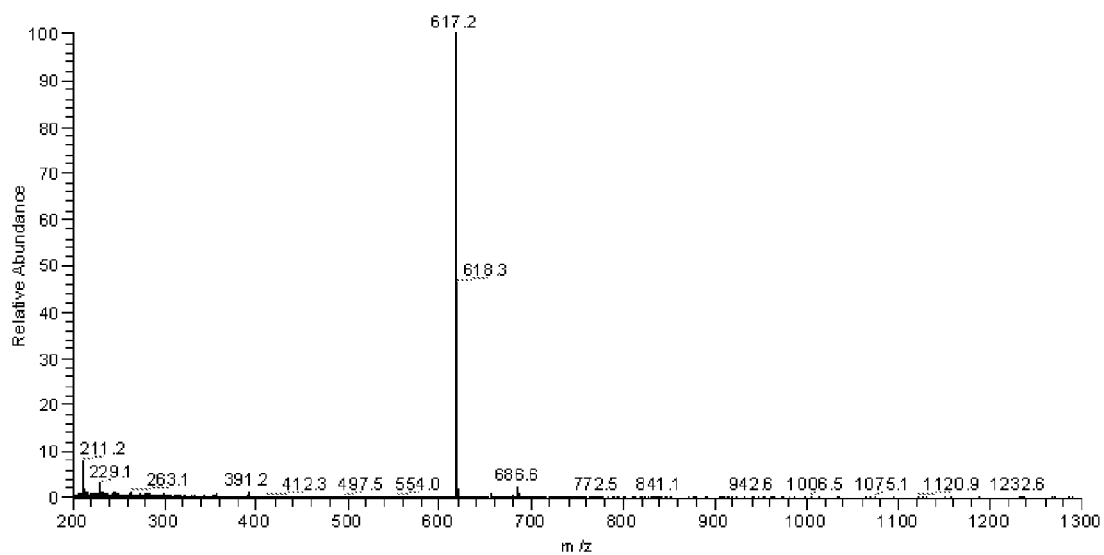
FIG. 5 is an NMR graph of the compound of Structural Formula 31 synthesized in Preparation Example 3.
Figure 6:
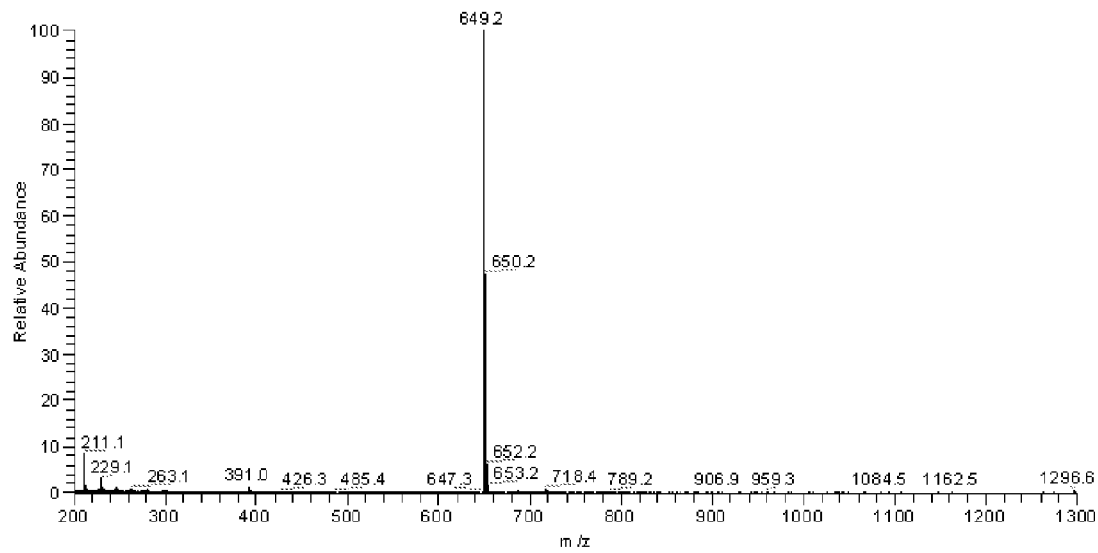
FIG. 6 is an NMR graph of the compound of Structural Formula 32 synthesized in Preparation Example 4.

For example, the structure of the organic light emitting device of the present specification may have a structure shown in FIG. 1 and FIG. 2, but the structure is not limited thereto.

FIG. 1 illustrates the structure of an organic electronic device in which an anode (2), a light emitting layer (3) and a cathode (4) are laminated on a substrate (1) in consecutive order. In this structure, the compound may be included in the light emitting layer (3).

FIG. 2 illustrates the structure of an organic electronic device in which an anode (2), a hole injection layer (5), a hole transfer layer (6), a light emitting layer (7), an electron transfer layer (8) and a cathode (4) are laminated on a substrate (1) in consecutive order. In this structure, the compound may be included in the hole injection layer (5), the hole transfer layer (6), the light emitting layer (7) or the electron transfer layer (8).

The compound according to one embodiment of the present specification may be used in the organic material layer of an organic light emitting device, and more specifically, in the hole injection layer material, the hole transfer layer material, the light emitting layer material or the electron transfer layer material.

The material used in an organic light emitting device is mostly a pure organic material or a complex compound in which a organic material and a metal form a complex, and can be categorized into a hole injection material, a hole transfer material, a light emitting material, an electron transfer material, an electron injection material and the like depending on the application.

Herein, as the hole injection material or the hole transfer material, an organic material having p-type characteristics, that is, an organic material that is easily oxidized and is in stable condition electrochemically when oxidized is normally used.

On the other hand, as the electron injection material or the electron transfer material, an organic material having n-type characteristics, that is, an organic material that is easily reduced and is in stable condition electrochemically when reduced is normally used.

As the light emitting layer material, a material having both p-type characteristics and n-type characteristics, that is, a material that has a stable form in both oxidized and reduced states is preferable, and a material having high light emission efficiency, which means converting excitons to light, when excitons are formed.

The compound according to the present specification is easily oxidized, and is stable electrochemically when oxidized, thereby is preferable to be used as the hole injection material or the hole transfer material.

The compound according to the present specification is easily reduced, and is stable electrochemically when reduced, thereby is preferable to be used as the electron transfer material.

The compound according to the present specification is stable in both oxidized and reduced states, and has high light emission efficiency, which means converting excitons to light, when excitons are formed, thereby is preferable to be used as the light emitting layer material.

In order to obtain a highly efficient organic light emitting device that can drive at a low voltage, the holes or the electrons injected into the organic light emitting device need to be smoothly transferred to the light emitting layer, and at the same time, the injected holes and electrons need to be kept so as not to escape outside the light emitting layer. For this, the material that is used in the organic light emitting device needs to have a suitable band gap, and a suitable HOMO or LUMO energy level.

The compound according to the present specification has an advantage in that the compound has a suitable HOMO or LUMO level so that the holes or the electrons are smoothly transferred to the light emitting layer, and at the same time, the injected holes and electrons do not escape outside the light emitting layer.

The compound according to the present specification has an advantage in that the chemical stability is excellent.

The compound according to the present specification has advantages in that the formation of excitons is maximized so that the density of holes and electrons is balanced in the light emitting layer of an organic light emitting device by the compound having suitable hole or electron mobility.

The compound according to the present specification has an advantage in that there are few material deformations by moisture or oxygen.

The compound according to the present specification has an advantage in that the interface with an electrode including a metal or a metal oxide is made to be favorable for the stability of a device.

An organic solar cell according to the present specification may have a constitution including a first electrode, a second electrode, and an organic material layer disposed therebetween, and may include a hole transfer layer, a photoactive layer and an electron transfer layer as the organic material layer. The compound according to one embodiment of the present application may be used in the organic material layer of the organic solar cell, and more specifically, in the electron transfer layer.

An organic photo conductor according to the present specification may include a conductive substrate, a charge transfer layer that includes an electron transfer material, and a charge generation layer. The compound according to one embodiment of the present application may be used in the charge transfer layer of the organic photo conductor.

An organic transistor according to the present specification may include a first electrode, a second electrode, a hole injection layer, an organic thin film layer, an electron injection layer, an electron transfer layer and the like. The compound according to one embodiment of the present application may be used in the electron transfer layer of the organic transistor.

Hereinafter, a method for preparing the compound of Chemical Formula 1 and manufacture of an organic electronic device using these compounds will be described in detail with reference to examples. However, the following examples are for illustrative purposes only, and the scope of the present specification is not limited thereto.

EXAMPLE

Preparation Example 1

Preparation of Structural Formula 29

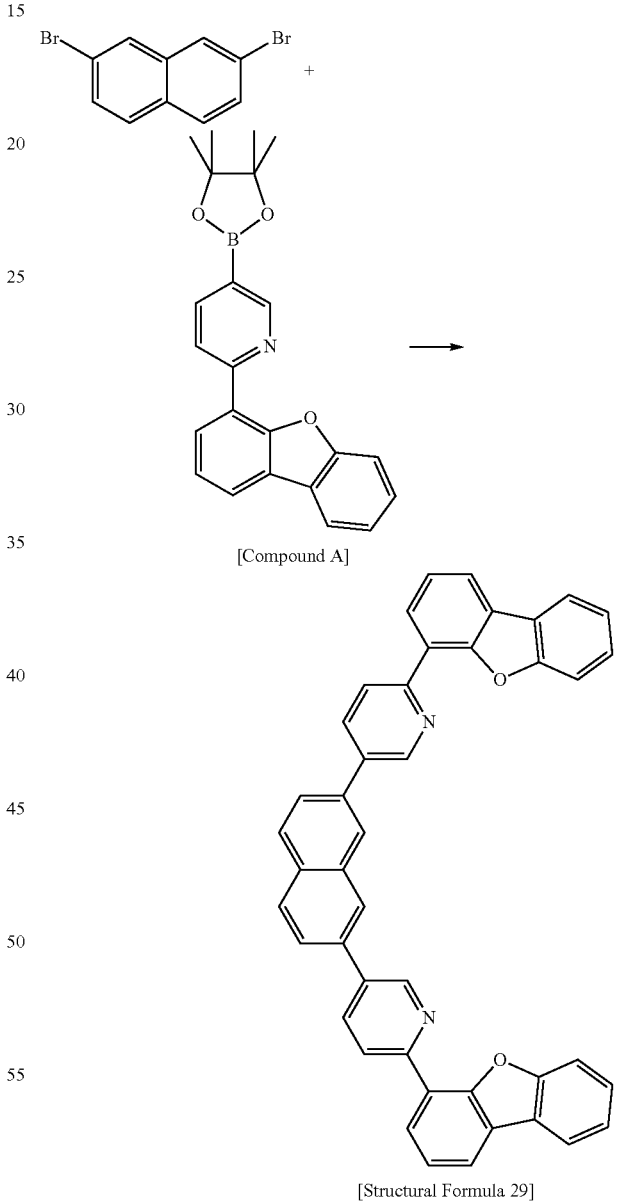

After 2,7-dibromonaphthalene (5.9 g, 20.7 mmol) and Compound A (16.9 g, 45.5 mmol) were completely dissolved in tetrahydrofuran (THF, 100 mL), a 2 M aqueous potassium carbonate solution (50 mL) and then Pd(PPh$_3$)$_4$ (0.7 g, 3 mol %) were added thereto, and the mixture was stirred under reflux for 24 hours. The temperature was lowered to room temperature, the water layer was removed, and the organic layer was filtered. The solid was adsorbed to silica gel and columned, and Structural Formula 29 (6.7 g, 53%) was obtained.

MS: [M+H]$^+$ =615

Preparation Example 2

Preparation of Structural Formula 30

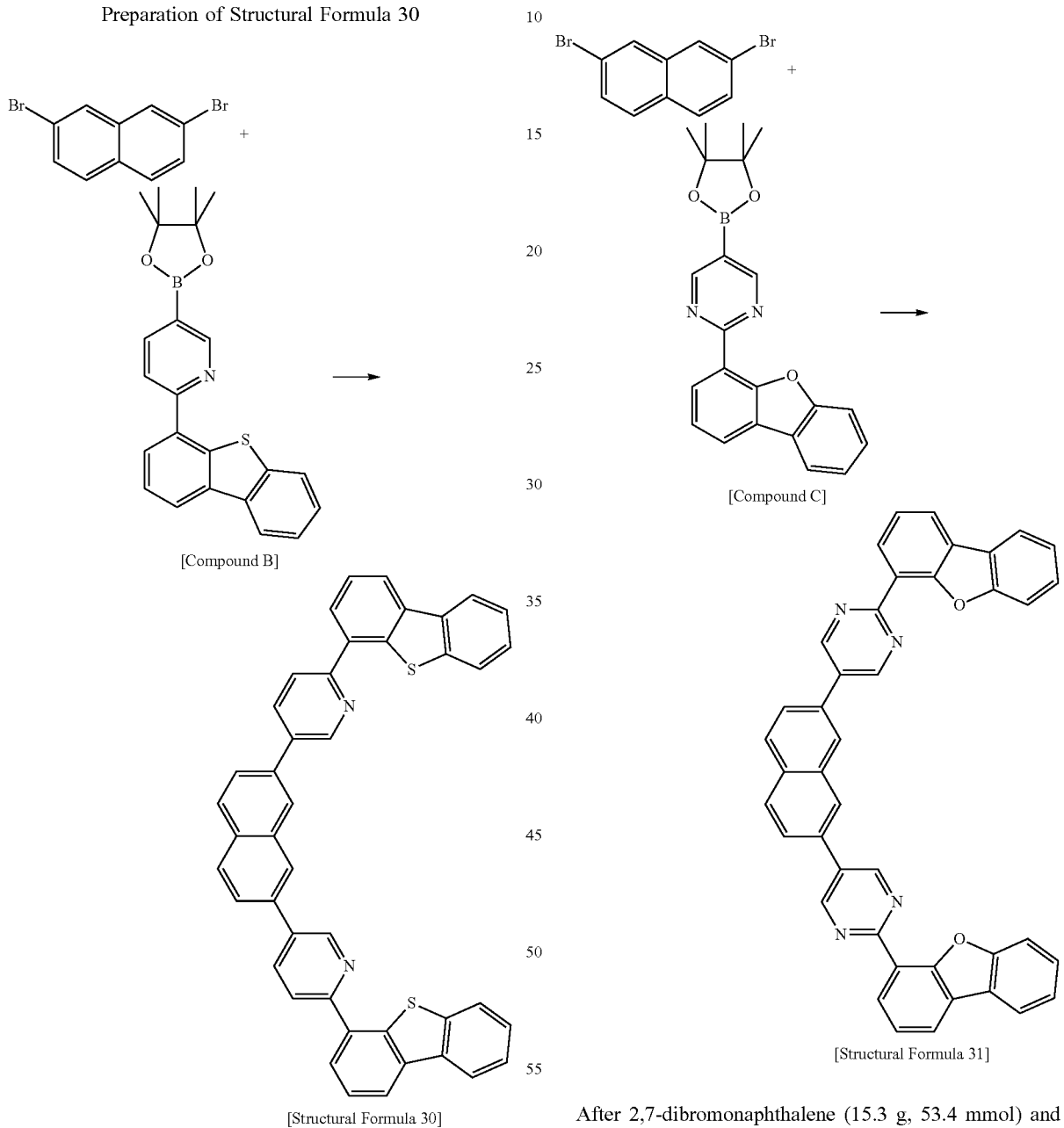

[Compound B]

[Structural Formula 30]

After 2,7-dibromonaphthalene (5.7 g, 20.0 mmol) and Compound B (17.0 g, 43.9 mmol) were completely dissolved in tetrahydrofuran (THF, 100 mL), a 2 M aqueous potassium carbonate solution (50 mL) and then Pd(PPh$_3$)$_4$ (0.7 g, 3 mol %) were added thereto, and the mixture was stirred under reflux for 24 hours. The temperature was lowered to room temperature, the water layer was removed, and the organic layer was filtered. The solid was adsorbed to silica gel and columned, and Structural Formula 30 (6.0 g, 46%) was obtained.

MS: [M+H]$^+$ =647

Preparation Example 3

Preparation of Structural Formula 31

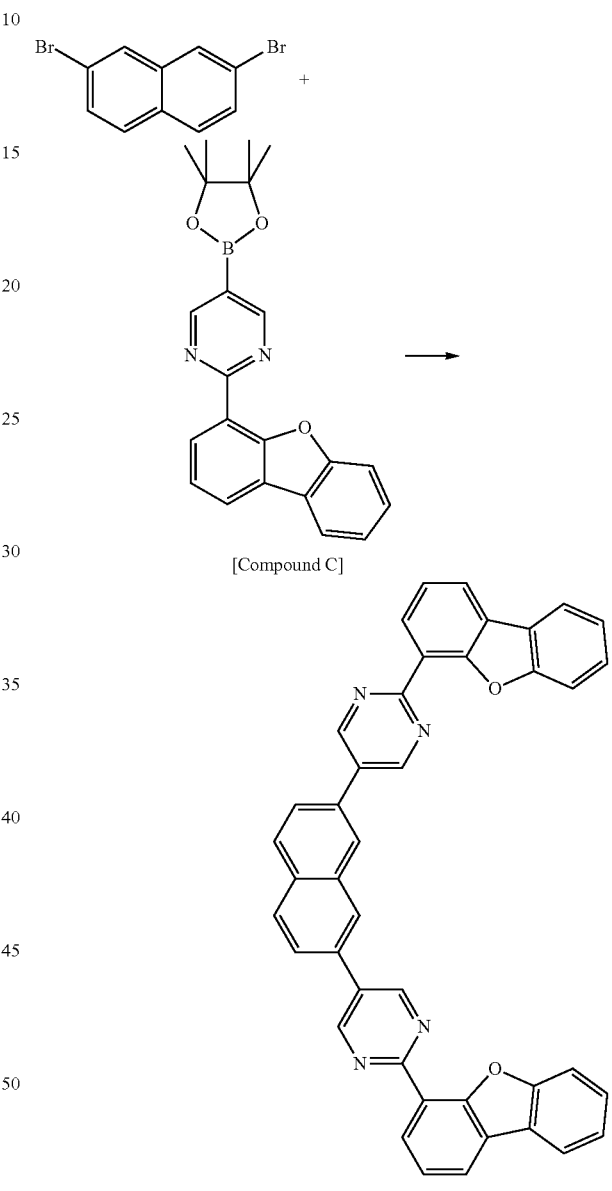

[Compound C]

[Structural Formula 31]

After 2,7-dibromonaphthalene (15.3 g, 53.4 mmol) and Compound C (43.8 g, 118 mmol) were completely dissolved in tetrahydrofuran (THF, 100 mL), a 2 M aqueous potassium carbonate solution (50 mL) and then Pd(PPh$_3$)$_4$ (1.9 g, 3 mol %) were added thereto, and the mixture was stirred under reflux for 24 hours. The temperature was lowered to room temperature, the water layer was removed, and the organic layer was filtered. The solid was adsorbed to silica gel and columned, and Structural Formula 31 (9.9 g, 30%) was obtained.

MS: [M+H]$^+$ =617

Preparation Example 4

Preparation of Structural Formula 32

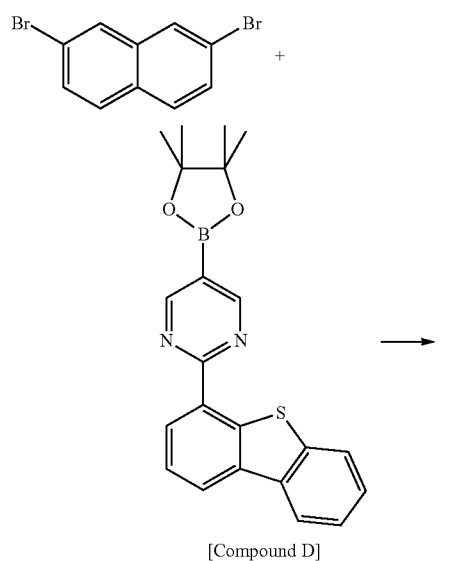

[Structural Formula 32]

After 2,7-dibromonaphthalene (4.4 g, 15.2 mmol) and Compound D (13.0 g, 33.5 mmol) were completely dissolved in tetrahydrofuran (THF, 100 mL), a 2 M aqueous potassium carbonate solution (50 mL) and then Pd(PPh$_3$)$_4$ (0.5 g, 3 mol %) were added thereto, and the mixture was stirred under reflux for 24 hours. The temperature was lowered to room temperature, the water layer was removed, and the organic layer was filtered. The solid was adsorbed to silica gel and columned, and Structural Formula 32 (5.6 g, 56%) was obtained.

MS: [M+H]$^+$ =649

Preparation Example 5

Preparation of Structural Formula 41

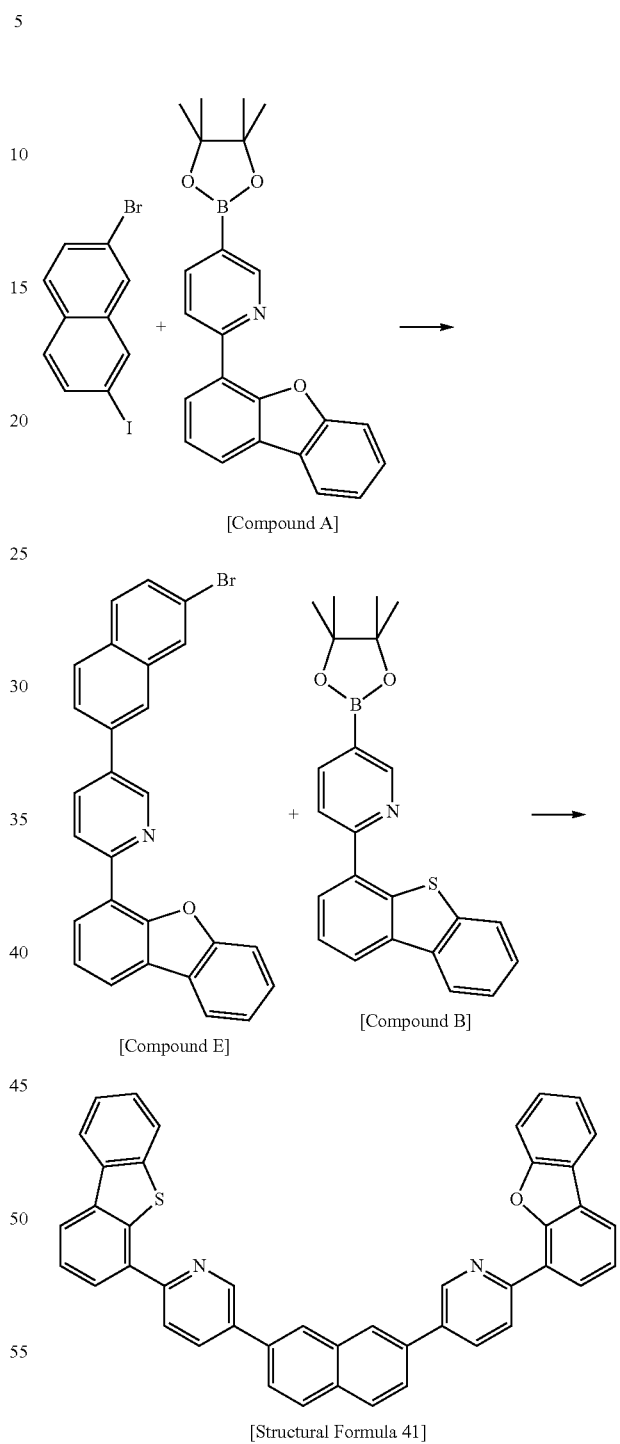

[Structural Formula 41]

After 2-bromo-7-iodonaphthalene (30 g, 90.1 mmol) and Compound A (33.4 g, 90.1 mmol) were completely dissolved in tetrahydrofuran (THF, 300 mL), a 2 M aqueous potassium carbonate solution (50 mL) and then Pd(PPh$_3$)$_4$ (1.0 g, 1 mol %) were added thereto, and the mixture was stirred under reflux for 24 hours. The temperature was lowered to room temperature, the water layer was removed, and the organic layer was filtered. The solid was adsorbed to silica gel and columned, and Compound E (17.4 g, 43%) was obtained.

After Compound E (5 g, 11.1 mmol) and Compound B (4.3 g, 11.1 mmol) were completely dissolved in tetrahydrofuran (THF, 100 mL), a 2 M aqueous potassium carbonate solution (50 mL) and then Pd(PPh$_3$)$_4$ (0.38 g, 3 mol %) were added thereto, and the mixture was stirred under reflux for 24 hours. The temperature was lowered to room temperature, the water layer was removed, and the organic layer was filtered. The solid was adsorbed to silica gel and columned, and Structural Formula 41 (4.3 g, 32%) was obtained.

MS: [M+H]$^+$ =630

Preparation Example 6

Preparation of Structural Formula 42

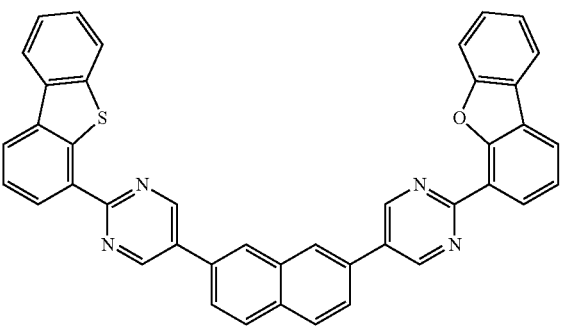

[Structural Formula 42]

After 2-bromo-7-iodonaphthalene (30 g, 90.1 mmol) and Compound C (33.5 g, 90.1 mmol) were completely dissolved in tetrahydrofuran (THF, 300 mL), a 2 M aqueous potassium carbonate solution (50 mL) and then Pd(PPh$_3$)$_4$ (1.0 g, 1 mol %) were added thereto, and the mixture was stirred under reflux for 24 hours. The temperature was lowered to room temperature, the water layer was removed, and the organic layer was filtered. The solid was adsorbed to silica gel and columned, and Compound F (10.2 g, 25%) was obtained.

After Compound F (5.2 g, 11.5 mmol) and Compound D (4.5 g, 11.1 mmol) were completely dissolved in tetrahydrofuran (THF, 100 mL), a 2 M aqueous potassium carbonate solution (50 mL) and then Pd(PPh$_3$)$_4$ (0.38 g, 3 mol %) were added thereto, and the mixture was stirred under reflux for 24 hours. The temperature was lowered to room temperature, the water layer was removed, and the organic layer was filtered. The solid was adsorbed to silica gel and columned, and Structural Formula 42 (3.0 g, 41%) was obtained.

MS: [M+H]$^+$ =632

Preparation Example 7

Preparation of Structural Formula 43

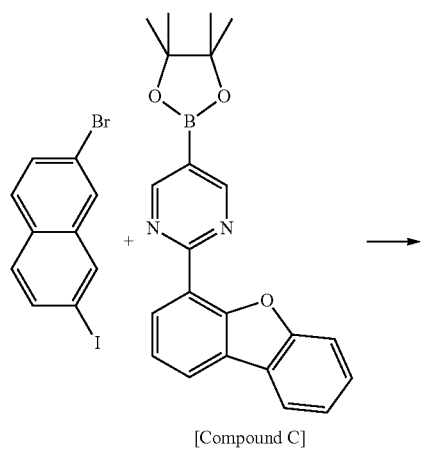

[Compound C]

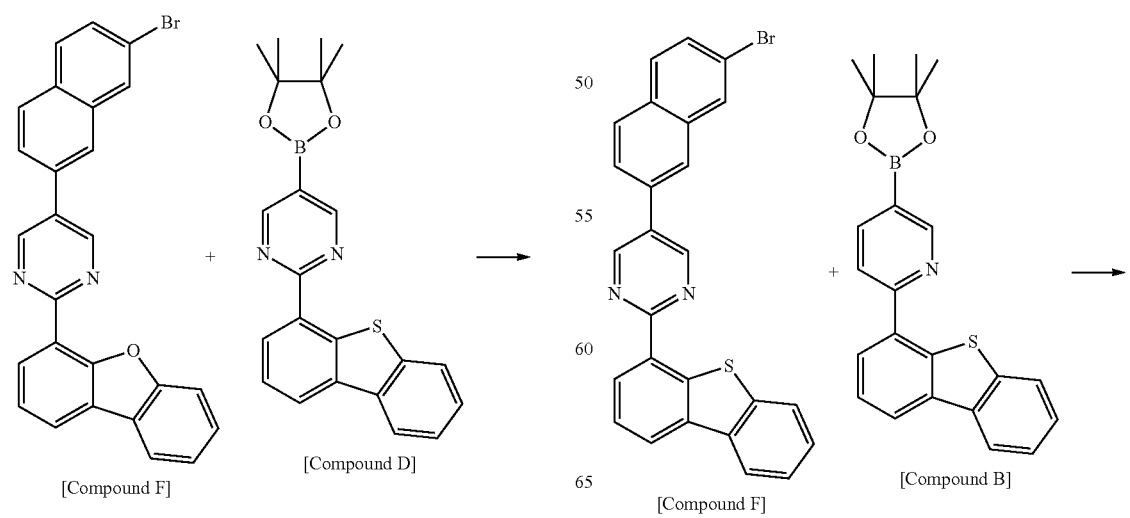

[Compound F]      [Compound D]      [Compound F]      [Compound B]

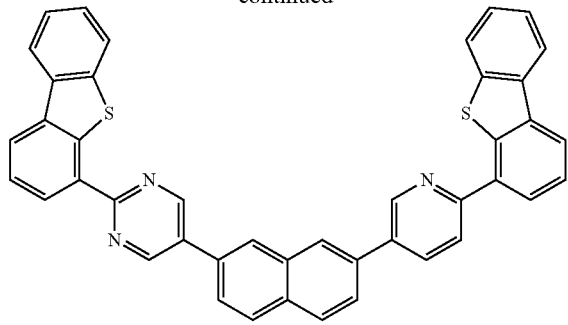

[Structural Formula 43]

After Compound F (6.5 g, 13.9 mmol) and Compound B (5.39 g, 13.9 mmol) were completely dissolved in tetrahydrofuran (THF, 100 mL), a 2 M aqueous potassium carbonate solution (50 mL) and then Pd(PPh$_3$)$_4$ (0.48 g, 3 mol %) were added thereto, and the mixture was stirred under reflux for 24 hours. The temperature was lowered to room temperature, the water layer was removed, and the organic layer was filtered. The solid was adsorbed to silica gel and columned, and Structural Formula 43 (1.7 g, 19%) was obtained.

MS: [M+H]$^+$ =647

Preparation Example 8

Preparation of Structural Formula 44

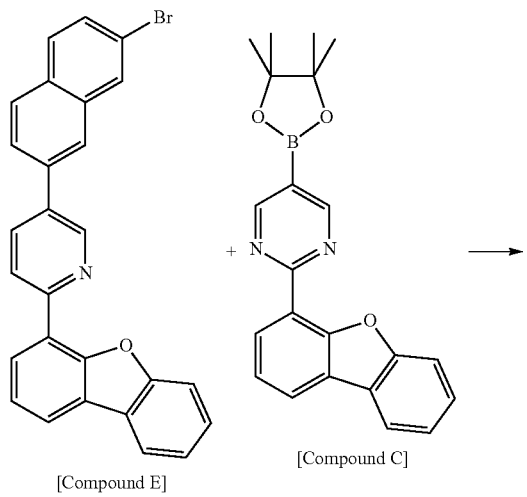

[Compound E]    [Compound C]

[Structural Formula 44]

After Compound E (6 g, 13.3 mmol) and Compound C (4.95 g, 11.1 mmol) were completely dissolved in tetrahydrofuran (THF, 100 mL), a 2 M aqueous potassium carbonate solution (50 mL) and then Pd(PPh$_3$)$_4$ (0.46 g, 3 mol %) were added thereto, and the mixture was stirred under reflux for 24 hours. The temperature was lowered to room temperature, the water layer was removed, and the organic layer was filtered. The solid was adsorbed to silica gel and columned, and Structural Formula 44 (2.94 g, 35%) was obtained.

MS: [M+H]$^+$ =631

Example 1

A glass substrate on which indium tin oxide (ITO) was coated as a thin film to a thickness of 500 Å was placed in distilled water in which a detergent was dissolved, and then was ultrasonic cleaned. At this time, a product of Fischer Corporation was used as the detergent, and as the distilled water, distilled water filtered twice with a filter manufactured by Millipore Corporation was used. After the ITO was cleaned for 30 minutes, ultrasonic cleaning was repeated twice for 10 minutes using distilled water. After the cleaning with distilled water was finished, ultrasonic cleaning was performed using an isopropyl alcohol solvent, an acetone solvent and a methanol solvent, and the substrate was dried and transferred to a plasma washer. In addition, the substrate was washed for 5 minutes using oxygen plasma, and then the substrate was transferred to a vacuum deposition apparatus.

On the transparent ITO electrode prepared as above, a hole injection layer was formed to a thickness of 500 Å by thermal vacuum depositing hexanitrile hexaazatriphenylene (HAT) of the following chemical formula.

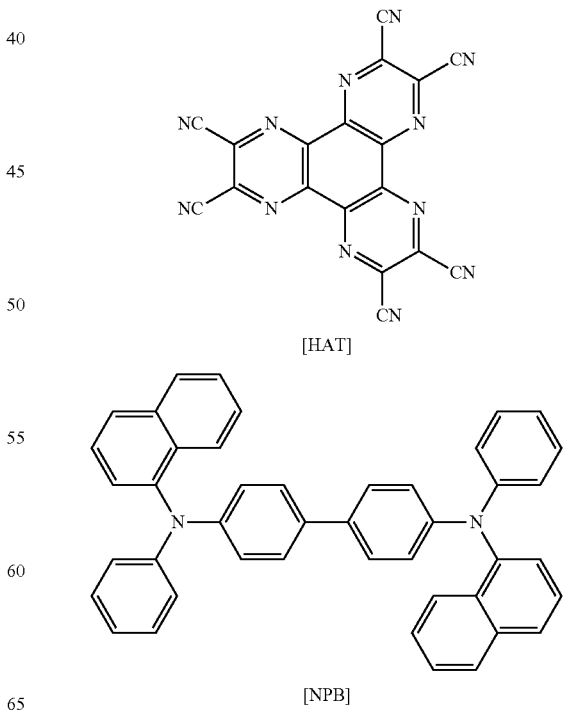

[HAT]

[NPB]

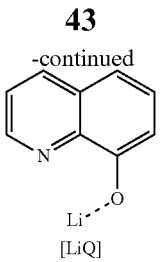

[LiQ]

On the hole injection layer, a hole injection layer, a hole transfer layer, a light emitting layer and an electron transfer layer were formed in consecutive order by vacuum depositing 4-4'-bis[N-(1-naphthyl)-N-phenylamino]biphenyl (NPB) (250 Å), hexanitrile hexaazatriphenylene (HAT) (50 Å), 4-4'-bis[N-(1-naphthyl)-N-phenylamino]biphenyl (NPB) (400 Å), $Alq_3$ (300 Å), and then by thermal vacuum depositing the compound of Structural Formula 29 prepared in the preparation example described above and Lithium Quinalate (LiQ) in the weight ratio of 1:1 to a thickness of 300 Å.

A cathode was formed on the electron transfer layer by depositing lithium fluoride (LiF) to a thickness of 12 Å and aluminum to a thickness of 2,000 Å in consecutive order, and as a result, an organic light emitting device was manufactured.

In the above process, the deposition rate of the organic material was maintained to be 0.4 to 0.7 Å/sec, the deposition rate of the lithium fluoride of the cathode to be 0.3 Å/sec, and the deposition rate of the aluminum to be 2 Å/sec, and the degree of vacuum when being deposited was maintained to be $2 \times 10^{-7}$ to $5 \times 10^{-8}$ torr.

When a forward direction electric field of 6V was applied to the device manufactured as above, the results of the following Table 1 were obtained.

Example 2

The organic light emitting device was manufactured using the same method as in Example 1 except that the compound of Structural Formula 30 synthesized in Preparation Example 2 was used instead of the compound of Structural Formula 29 of Example 1.

Example 3

The organic light emitting device was manufactured using the same method as in Example 1 except that the compound of Structural Formula 31 synthesized in Preparation Example 3 was used instead of the compound of Structural Formula 29 of Example 1.

Example 4

The organic light emitting device was manufactured using the same method as in Example 1 except that the compound of Structural Formula 32 synthesized in Preparation Example 4 was used instead of the compound of Structural Formula 29 of Example 1.

Example 5

The organic light emitting device was manufactured using the same method as in Example 1 except that the compound of Structural Formula 41 synthesized in Preparation Example 5 was used instead of the compound of Structural Formula 29 of Example 1.

Example 6

The organic light emitting device was manufactured using the same method as in Example 1 except that the compound of Structural Formula 42 synthesized in Preparation Example 6 was used instead of the compound of Structural Formula 29 of Example 1.

Example 7

The organic light emitting device was manufactured using the same method as in Example 1 except that the compound of Structural Formula 43 synthesized in Preparation Example 7 was used instead of the compound of Structural Formula 29 of Example 1.

Example 8

The organic light emitting device was manufactured using the same method as in Example 1 except that the compound of Structural Formula 44 synthesized in Preparation Example 8 was used instead of the compound of Structural Formula 29 of Example 1.

Comparative Example

A glass substrate (corning 7059 glass) on which indium tin oxide (ITO) was coated as a thin film to a thickness of 1,000 Å was placed in distilled water in which a detergent is dissolved, and then was ultrasonic cleaned. At this time, a product of Fischer Corporation was used as the detergent, and as the distilled water, distilled water filtered twice with a filter manufactured by Millipore Corporation was used. After the ITO was cleaned for 30 minutes, ultrasonic cleaning was repeated twice for 10 minutes using distilled water. After the cleaning with distilled water was finished, ultrasonic cleaning was performed using an isopropyl alcohol solvent, an acetone solvent and a methanol solvent in this order, and the substrate was dried.

On the ITO electrode, a hole injection layer, a hole transfer layer, a light emitting layer, and an electron transfer layer were formed in consecutive order by depositing hexanitrile hexaazatriphenylene (500 Å), 4-4'-bis[N-(1-naphthyl)-N-phenylamino]biphenyl (NPB) (400 Å) and $Alq_a$ (300 Å), and then by thermal vacuum depositing the following ET-A and Lithium Quinalate (LiQ) in the weight ratio of 1:1 (300 Å). On the electron transfer layer, a cathode was formed by depositing lithium fluoride (LiF) to a thickness of 12 Å and aluminum to a thickness of 2,000 Å in consecutive order, and as a result, an organic electronic device was manufactured.

In the above process, the deposition rate of the organic material was maintained to be 0.4 to 0.7 Å/sec, the deposition rate of the lithium fluoride of the cathode to be 0.3 Å/sec, and the deposition rate of the aluminum to be 2 Å/sec, and the degree of vacuum when being deposited was maintained to be $2 \times 10^{-7}$ to $5 \times 10^{-8}$ torr.

When a forward direction electric field of 6V was applied to the device manufactured as above, the results of the following Table 1 were obtained.

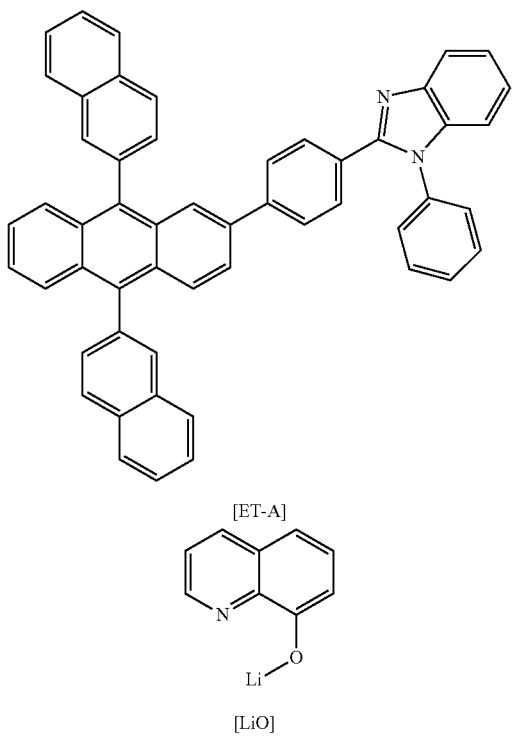

[ET-A]

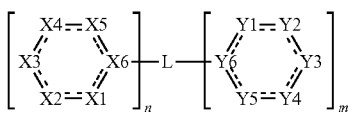

[LiO]

TABLE 1

|  | Compound | Voltage (V) | Efficiency (cd/A) |
| --- | --- | --- | --- |
| Example 1 | Structural Formula 29 | 4.1 | 5.8 |
| Example 2 | Structural Formula 30 | 4.0 | 6.1 |
| Example 3 | Structural Formula 31 | 4.1 | 6.0 |
| Example 4 | Structural Formula 32 | 4.2 | 6.8 |
| Example 5 | Structural Formula 41 | 4.1 | 5.9 |
| Example 6 | Structural Formula 42 | 4.2 | 6.0 |
| Example 7 | Structural Formula 43 | 4.1 | 6.0 |
| Example 8 | Structural Formula 44 | 4.2 | 6.2 |
| Comparative Example 1 | ET-A | 4.3 | 3.3 |

From the results of Table 1, it was seen that the new compounds according to the present invention can be used as an electron transfer layer material of an organic electronic device including an organic light emitting device, and the organic electronic device including an organic light emitting device using the compound shows excellent characteristics in efficiency, driving voltage, stability and the like.

The invention claimed is:

1. A compound represented by the following Chemical Formula 1:

[Chemical Formula 1]

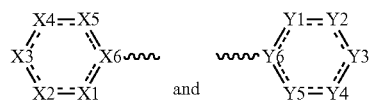

wherein, in Chemical Formula 1,
X1 to X5 and Y1 to Y5 are each independently C-Cy, N-Cy, CR or N;
X6 and Y6 are each independently C or N;
at least one of X1 to X6 is N, at least one of X1 to X5 is C-Cy or N-Cy;
at least one of Y1 to Y6 is N, at least one of Y1 to Y5 is C-Cy or N-Cy;
when X6 is N, at least one of X1 to X5 is C-Cy or CR;
when Y6 is N, at least one of Y1 to Y5 is C-Cy or CR;
Cy is a substituted or unsubstituted benzothiophene group; a substituted or unsubstituted benzofuran group; a substituted or unsubstituted dibenzothiophene group; or a substituted or unsubstituted dibenzofuran group;
R is hydrogen; deuterium; a halogen group; a nitro group; a hydroxy group; a substituted or unsubstituted alkyl group; a substituted or unsubstituted cycloalkyl group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group;
n and m are each independently an integer of 1 to 5;
n+m is 2 to 6; and
L is a substituted or unsubstituted aryl group having the valency of n+m.

2. The compound of claim 1, wherein

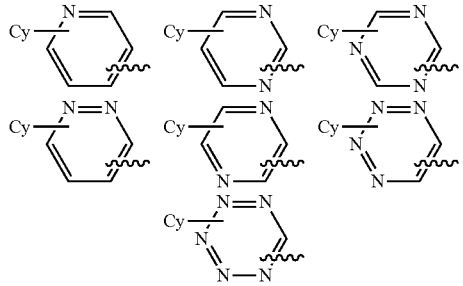

of Chemical Formula 1 are each independently represented by any one of the following chemical Formulae:

wherein, Cy is the same as that defined in Chemical Formula 1.

3. The compound of claim 1, wherein one or two of X1 to X6 is N or N-Cy.

4. The compound of claim 1, wherein one or two of Y1 to Y6 is N or N-Cy.

5. The compound of claim 1, wherein L is a substituted or unsubstituted phenyl group having the valency of n+m; a substituted or unsubstituted biphenyl group having the valency of n+m; a substituted or unsubstituted terphenyl group having the valency of n+m; a substituted or unsubstituted stilbene group having the valency of n+m; a substituted or unsubstituted naphthyl group having the valency of n+m; a substituted or unsubstituted anthracenyl group having the valency of n+m; a substituted or unsubstituted phenanthrene group having the valency of n+m; a substituted or unsubstituted pyrenyl group having the valency of n+m; a substituted or perylenyl group having the valency of n+m; a substituted or unsubstituted crycenyl group having the valency of n+m; or a substituted or unsubstituted fluorene group having the valency of n+m.

6. The compound of claim 1, wherein L is represented by any one of the following chemical formulae:

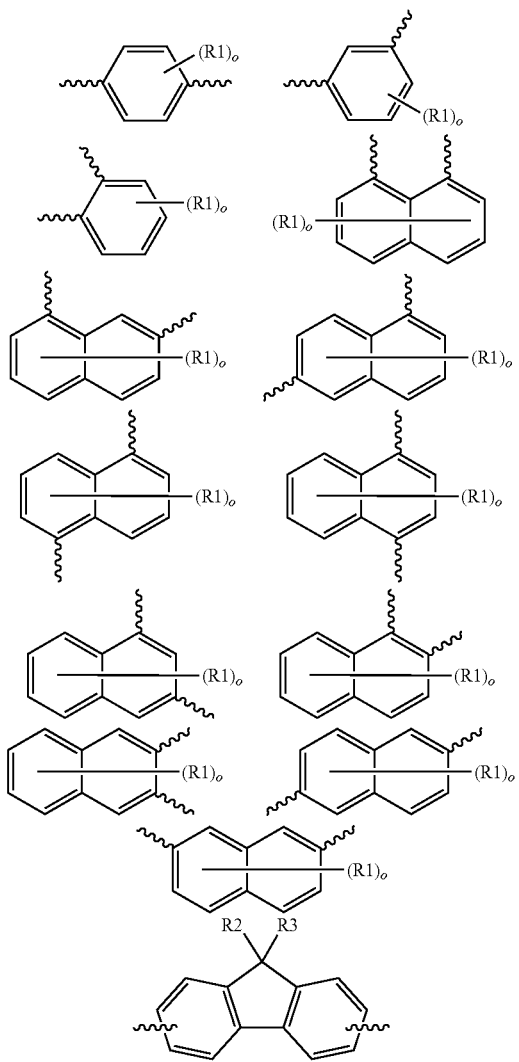

wherein, o is an integer of 0 to 4;
R1, R2 and R3 are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted heteroring group; or a substituted or unsubstituted fluorenyl group; and R1 to R3 form an aliphatic or a hetero fused ring with groups adjacent to each other.

7. The compound of claim 1, wherein n and m are 1.

8. The compound of claim 1, wherein the compound represented by Chemical Formula 1 is represented by any one of the following chemical formulae:

Structural Formula 1

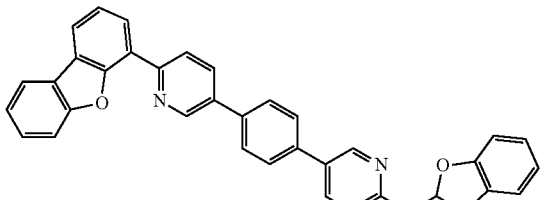

Structural Formula 2

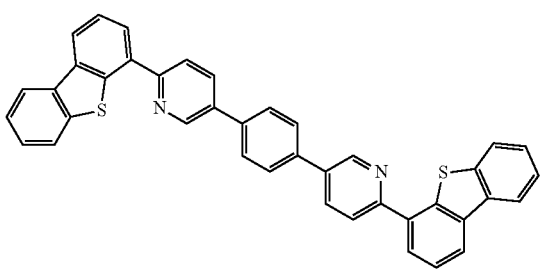

Structural Formula 3

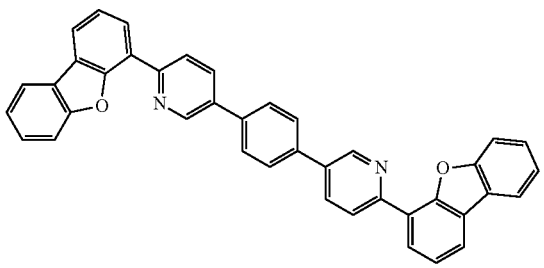

Structural Formula 4

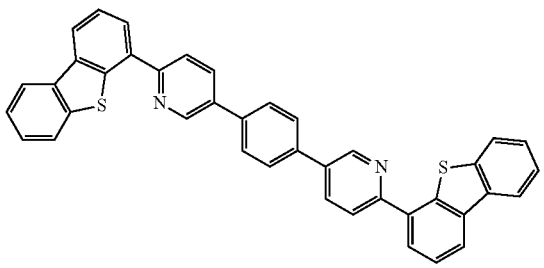

Structural Formula 5

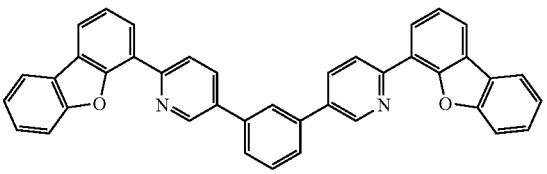

Structural Formula 6
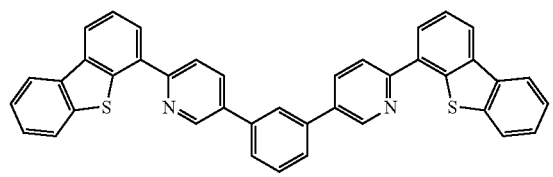
Structural Formula 7
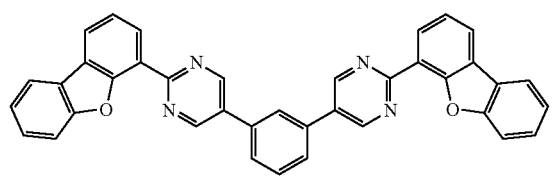
Structural Formula 8
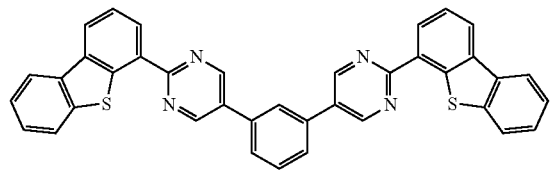
Structural Formula 9
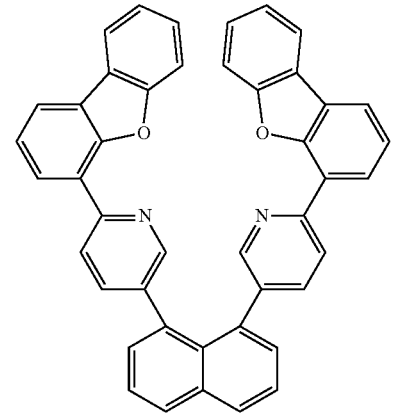
Structural Formula 10
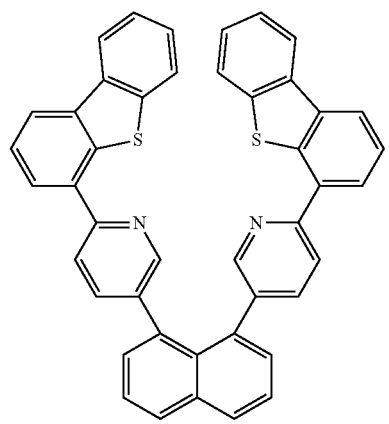
Structural Formula 11
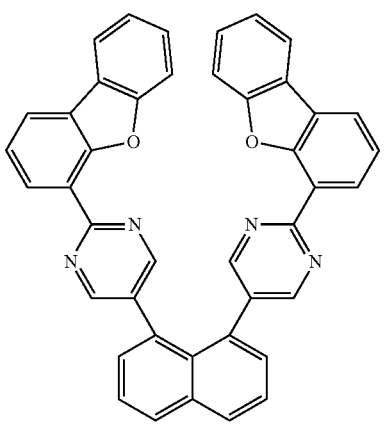
Structural Formula 12
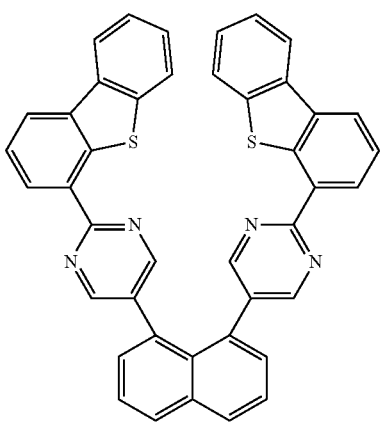
Structural Formula 13
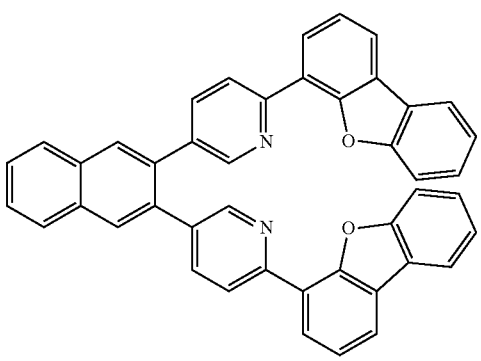
Structural Formula 14
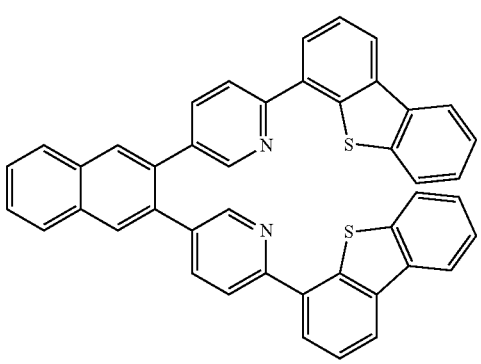

Structural Formula 15
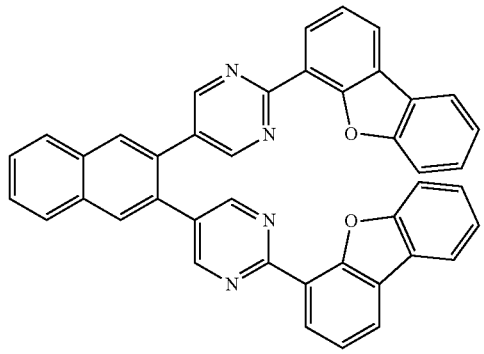
Structural Formula 16
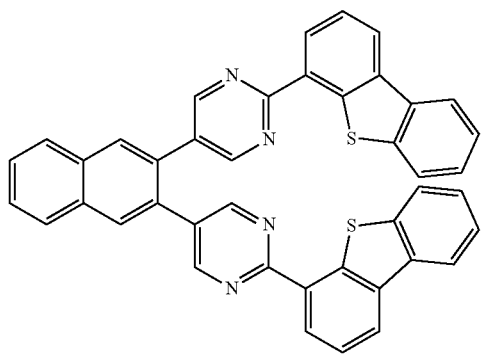
Structural Formula 17
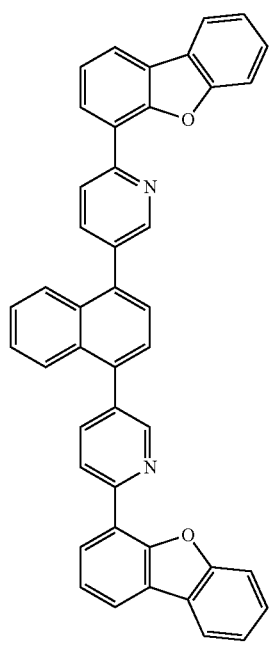
Structural Formula 18
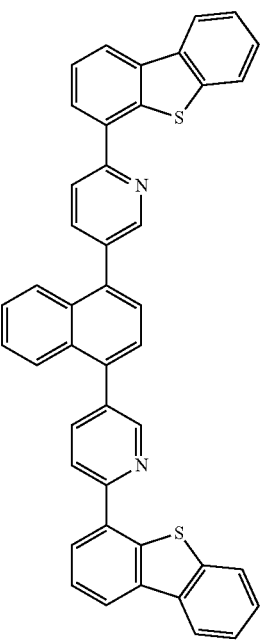
Structural Formula 19
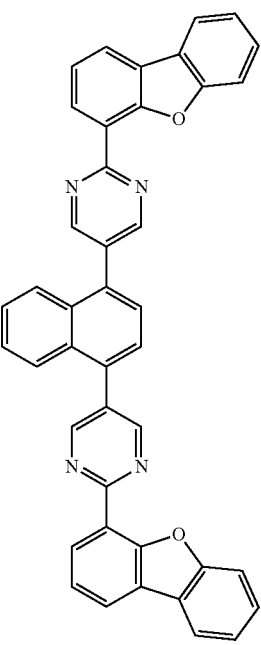

Structural Formula 20
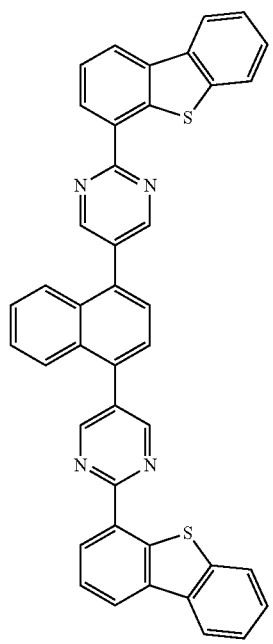
Structural Formula 21
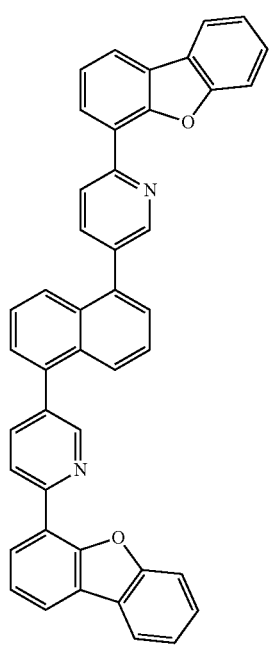
Structural Formula 22
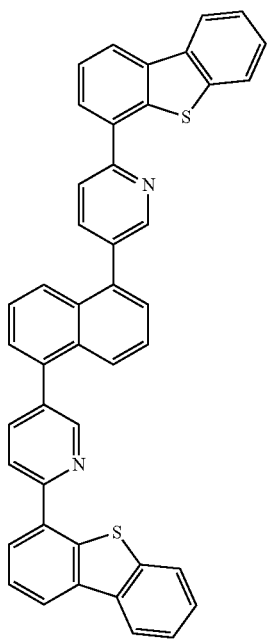
Structural Formula 23
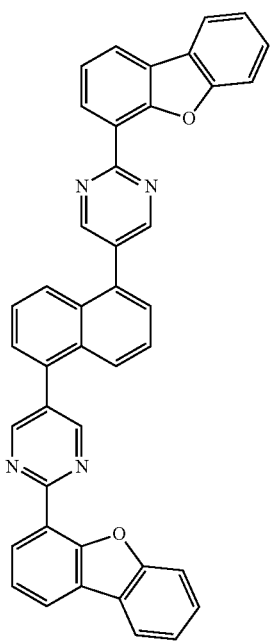

Structural Formula 24
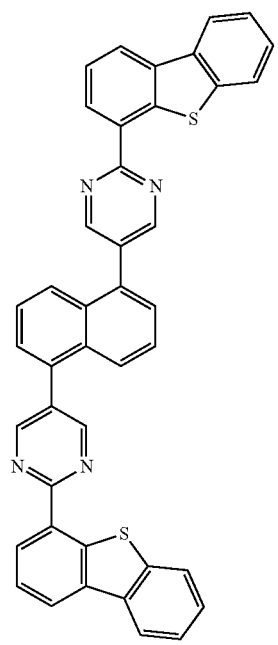
Structural Formula 26
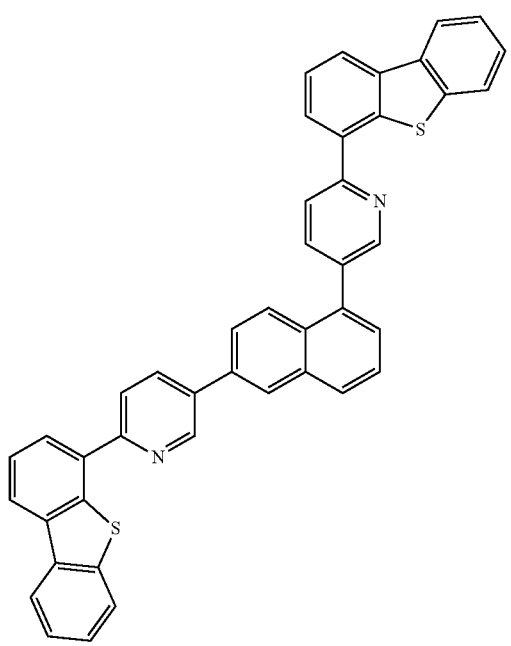
Structural Formula 25
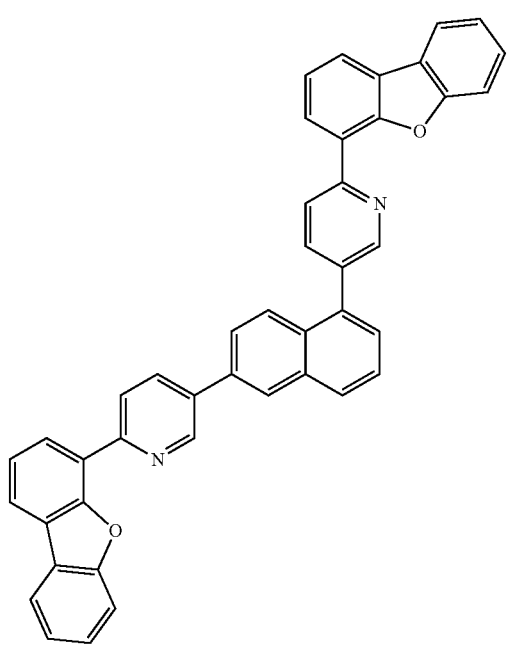
Structural Formula 27
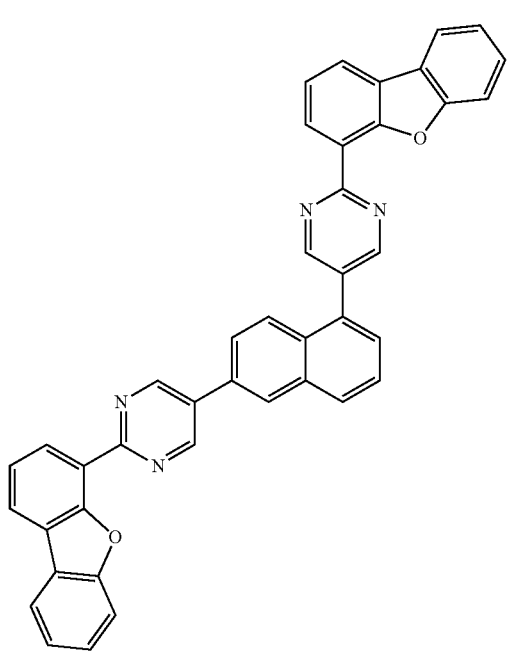

Structural Formula 28
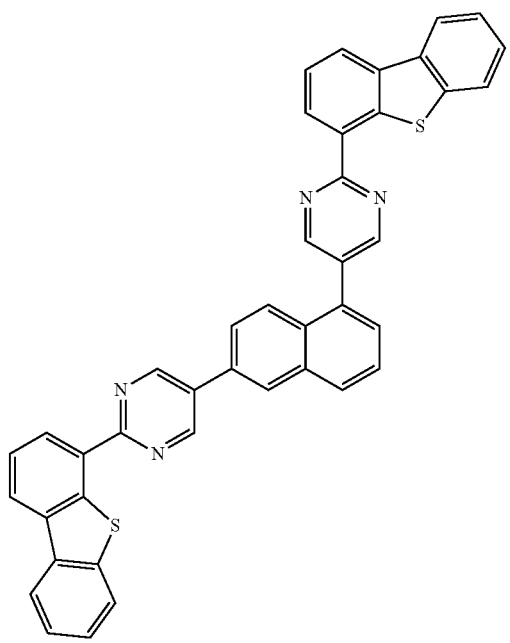
Structural Formula 29
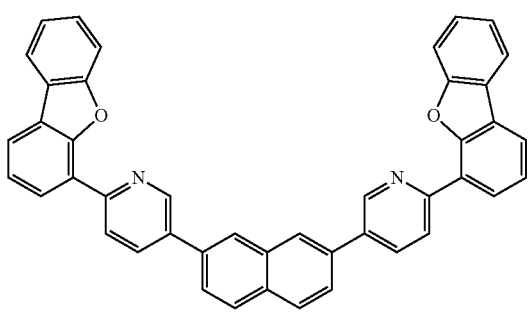
Structural Formula 30
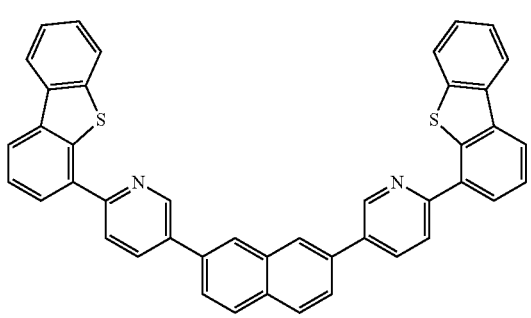
Structural Formula 31
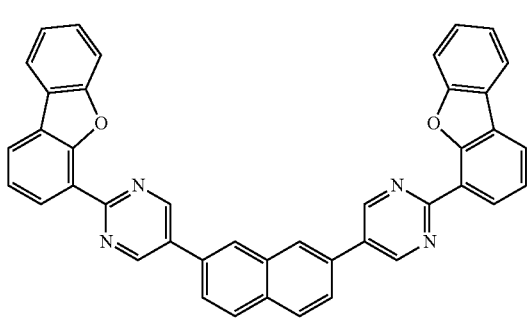
Structural Formula 32
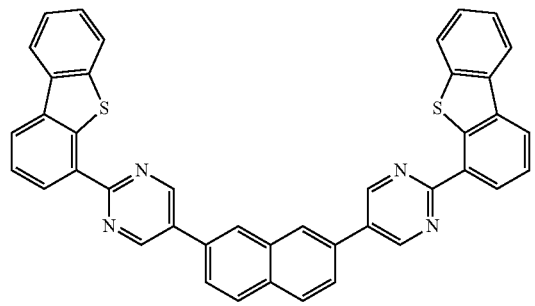
Structural Formula 33
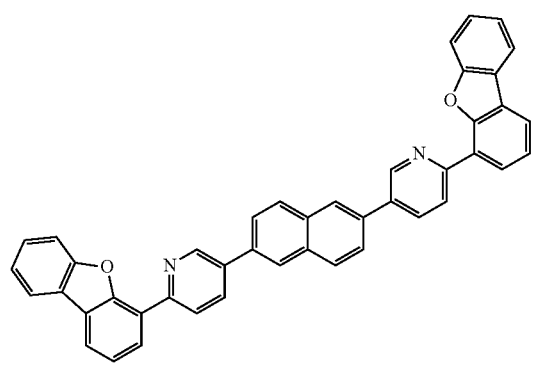
Structural 34
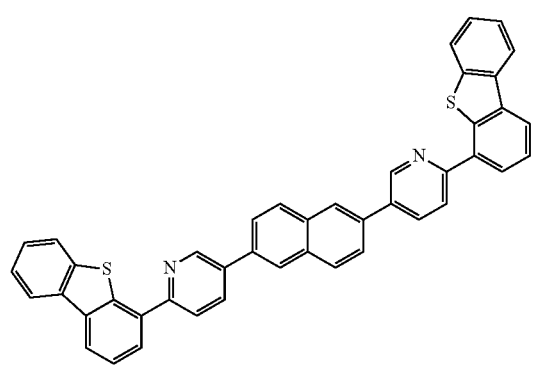
Structural 35
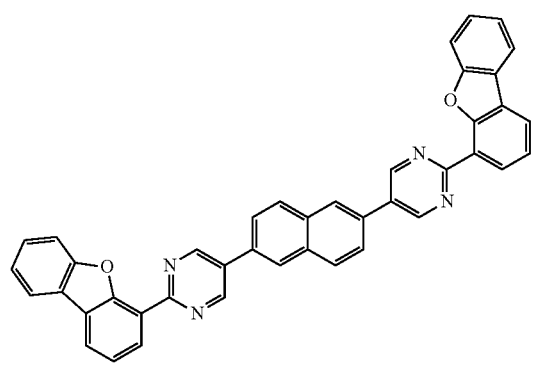

Structural Formula 36
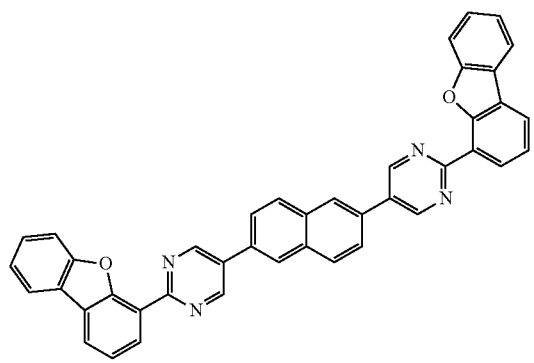
Structural Formula 37
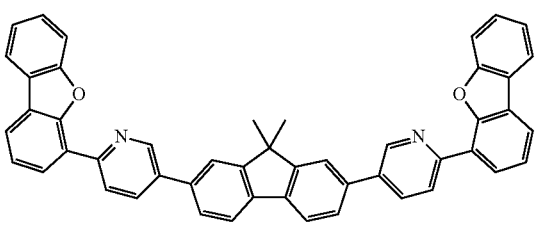
Structural Formula 38
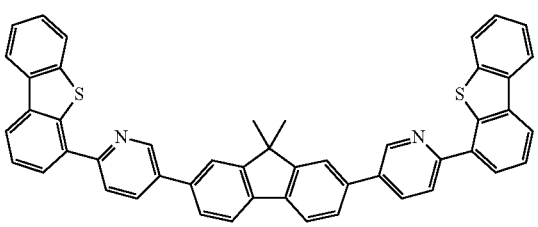
Structural Formula 39
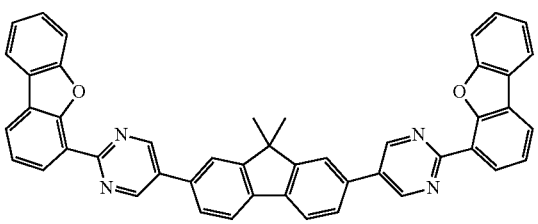
Structural Formula 40
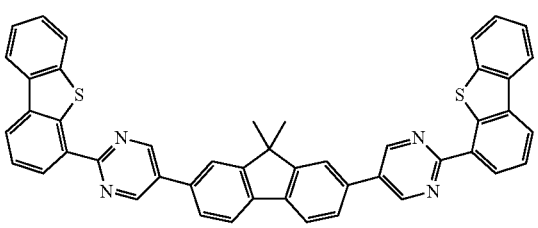
Structural Formula 41
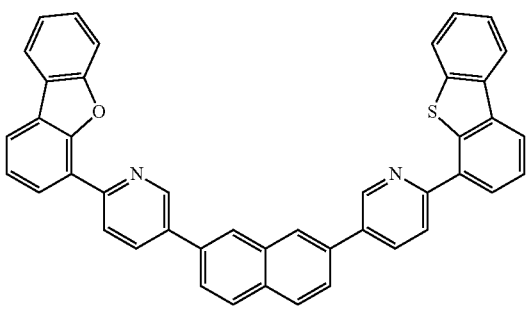
Structural Formula 42
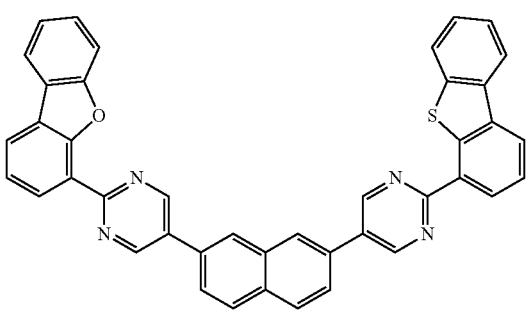
Structural Formula 43
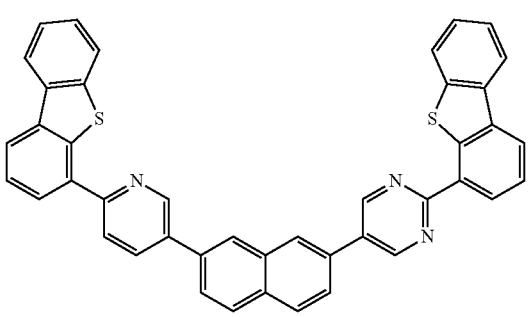
Structural Formula 44
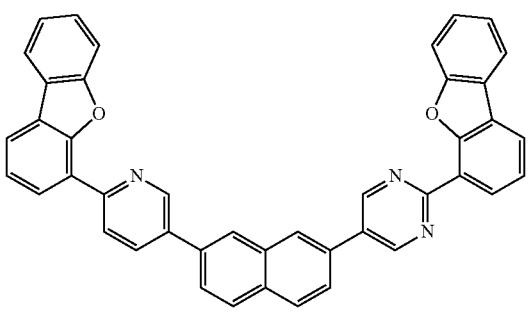
Structural Formula 45
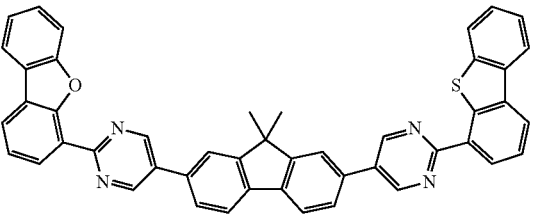

Structural Formula 46
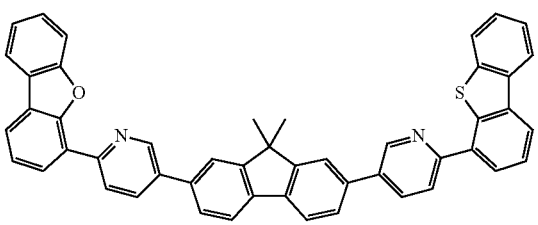
Structural Formula 47
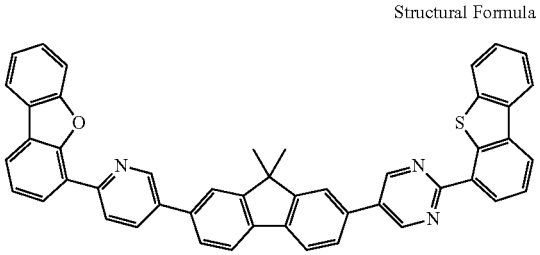
Structural Formula 48
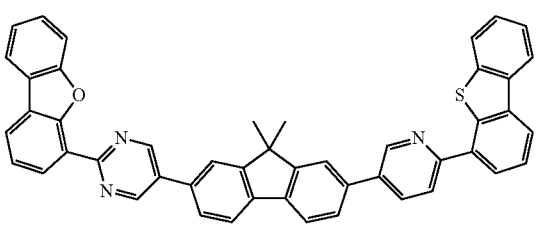
Structural Formula 49
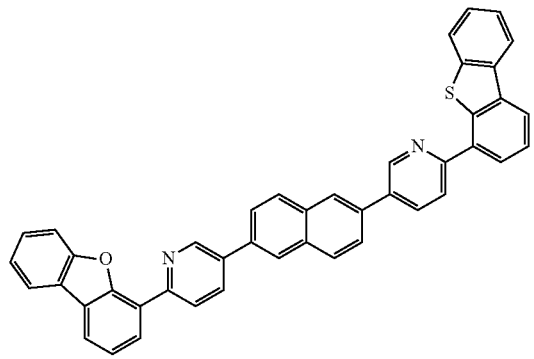
Structural Formula 50
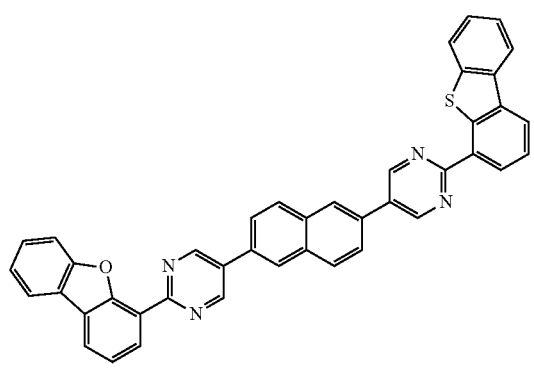
Structural Formula 51
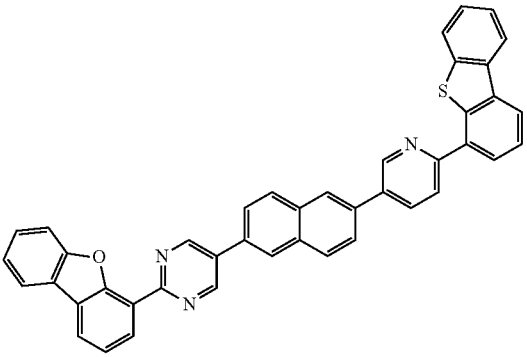
Structural Formula 52
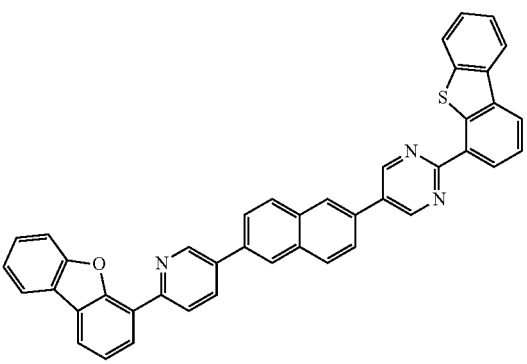
Structural Formula 53
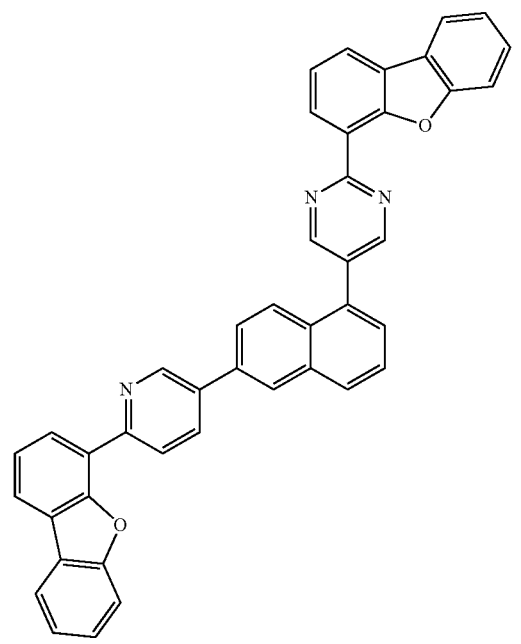

Structural Formula 54
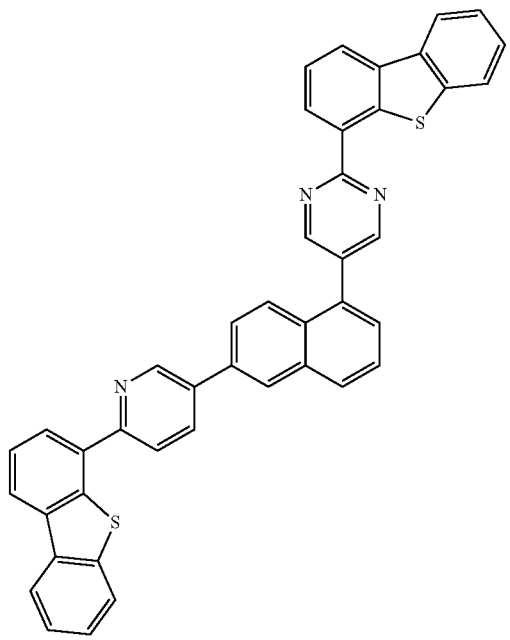
Structural Formula 56
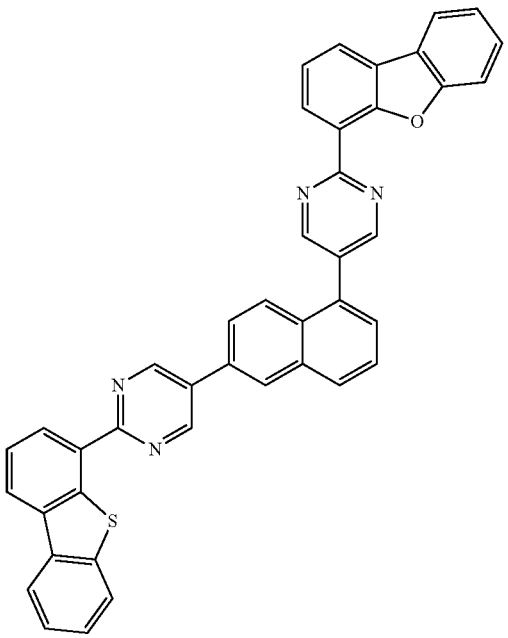
Structural Formula 55
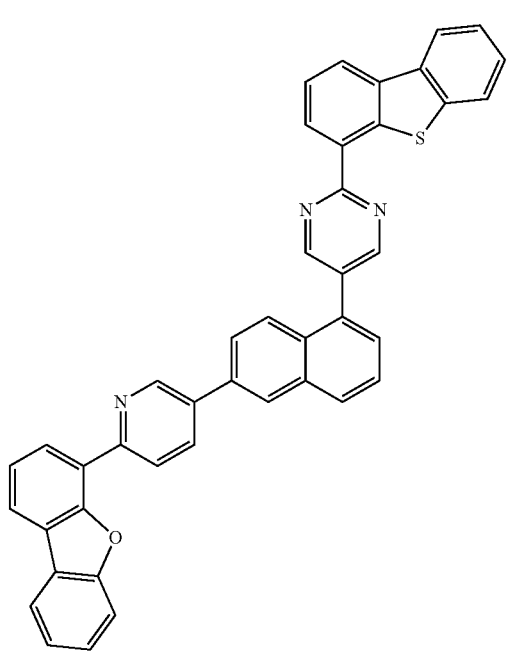
Structural Formula 57
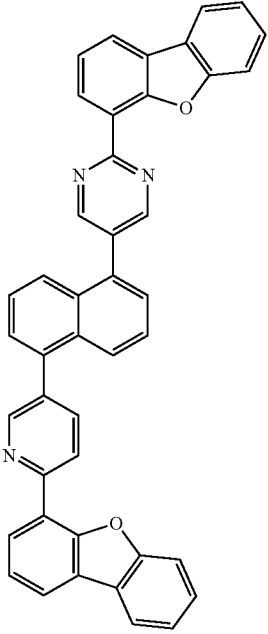

Structural Formula 58

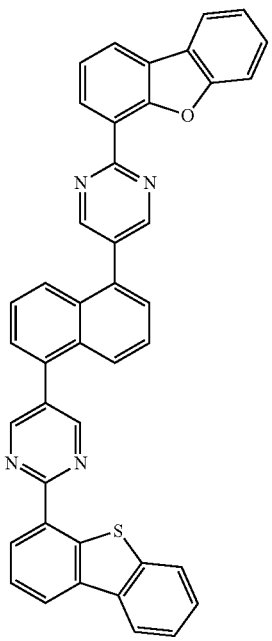

Structural Formula 59

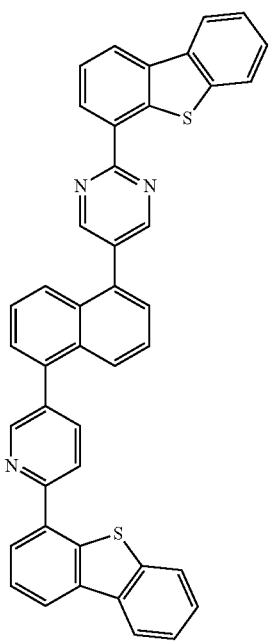

Structural Formula 60

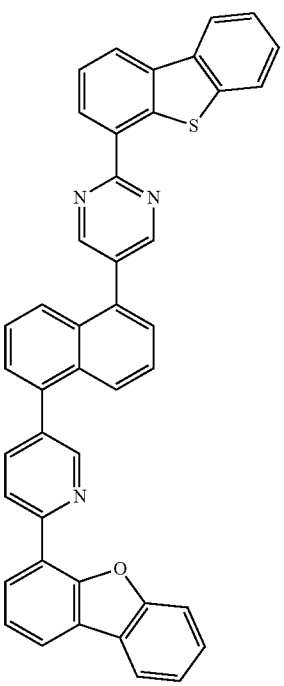

9. An organic electronic device comprising:
a first electrode;
a second electrode; and
one or more organic material layers provided between the first electrode and the second electrode,
wherein the one or more organic material layers include the compound of claim 1.

10. The organic electronic device of claim 9, wherein the organic material layer includes at least one of an electron blocking layer, an electron injection layer and an electron transfer layer, and at least one of the electron blocking layer, the electron injection layer and the electron transfer layer includes the compound.

11. The organic electronic device of claim 10, wherein the electron transfer layer includes the compound.

12. The organic electronic device of claim 9, wherein the organic material layer includes a light emitting layer, and the light emitting layer includes the compound.

13. An organic electronic device comprising:
a first electrode;
a second electrode; and
one or more organic material layers provided between the first electrode and the second electrode,
wherein the one or more organic material layers include the compound of claim 2.

14. An organic electronic device comprising:
a first electrode;
a second electrode; and
one or more organic material layers provided between the first electrode and the second electrode,
wherein the one or more organic material layers include the compound of claim 3.

15. An organic electronic device comprising:
a first electrode;
a second electrode; and
one or more organic material layers provided between the first electrode and the second electrode, wherein the one or more organic material layers include the compound of claim 4.

16. An organic electronic device comprising:
a first electrode;
a second electrode; and
one or more organic material layers provided between the first electrode and the second electrode,
wherein the one or more organic material layers include the compound of claim 5.

17. An organic electronic device comprising:
a first electrode;
a second electrode; and
one or more organic material layers provided between the first electrode and the second electrode,
wherein the one or more organic material layers include the compound of claim 6.

18. An organic electronic device comprising:
a first electrode;
a second electrode; and
one or more organic material layers provided between the first electrode and the second electrode,
wherein the one or more organic material layers include the compound of claim 7.

19. An organic electronic device comprising:
a first electrode;
a second electrode; and
one or more organic material layers provided between the first electrode and the second electrode,
wherein the one or more organic material layers include the compound of claim 8.

* * * * *